United States Patent
Singh et al.

(10) Patent No.: US 12,016,906 B2
(45) Date of Patent: Jun. 25, 2024

(54) PHARMACEUTICAL COMPOSITION FOR ANAEMIA

(71) Applicant: Frimline Private Limited, Gujarat (IN)

(72) Inventors: Ankit Shyam Singh, Gujarat (IN); Vedprakash Mishra, Gujarat (IN); Neelima Tongra, Rajasthan (IN)

(73) Assignee: Frimline Private Limited, Gujarat (IN)

( * ) Notice: Subject to any disclaimer, the term of this patent is extended or adjusted under 35 U.S.C. 154(b) by 919 days.

(21) Appl. No.: 16/978,989

(22) PCT Filed: Mar. 4, 2019

(86) PCT No.: PCT/IB2019/051706
§ 371 (c)(1),
(2) Date: Sep. 8, 2020

(87) PCT Pub. No.: WO2019/171236
PCT Pub. Date: Sep. 12, 2019

(65) Prior Publication Data
US 2020/0405822 A1    Dec. 31, 2020

(30) Foreign Application Priority Data
Mar. 9, 2018 (IN) .............................. 201821008809

(51) Int. Cl.
| | | |
|---|---|---|
| A61K 38/40 | (2006.01) | |
| A61K 9/16 | (2006.01) | |
| A61K 31/708 | (2006.01) | |
| A61K 33/26 | (2006.01) | |
| A61K 47/14 | (2017.01) | |
| A61K 47/22 | (2006.01) | |
| A61P 7/06 | (2006.01) | |

(52) U.S. Cl.
CPC ............ *A61K 38/40* (2013.01); *A61K 9/1617* (2013.01); *A61K 9/1682* (2013.01); *A61K 31/708* (2013.01); *A61K 33/26* (2013.01); *A61K 47/14* (2013.01); *A61K 47/22* (2013.01); *A61P 7/06* (2018.01)

(58) Field of Classification Search
None
See application file for complete search history.

(56) References Cited

FOREIGN PATENT DOCUMENTS

| | | |
|---|---|---|
| CN | 1218647 C | 9/2005 |
| CN | 106578134 A | 4/2017 |
| CN | 107549612 A | 1/2018 |
| WO | 2016/073132 A1 | 5/2016 |
| WO | WO-2016073132 A1 * | 5/2016 ............ A23L 33/115 |
| WO | 2018/009647 A1 | 1/2018 |
| WO | WO-2018009647 A1 * | 1/2018 ............ A23L 33/00 |

OTHER PUBLICATIONS

Heslett et al. Flier, "Breastmilk", Breastfeeding Course for Health Care Providers, Douglas Collage, British Columbia, Canada (Year: 2007).*
Anonymous "Ferronomic Plus" frimline.com/product/ferronomic-plus/ (Year: 2017).*
Anonymous "Ironemic Plus" frimline.com/product/ironemic-plus/ (Year: 2017).*
Anonymous "Ironemic" frimline.com/product/ironemic/ (Year: 2017).*
Theresa O. Scholl; article etitled "Iron status during pregnancy: setting the stage for mother and infant"; Am J Clin Nutr American Society for Clinical Nutrition; 2005; pp. 1218S-1222S.
Jay Umbreit; article entitled "Iron Deficiency: A Concise Review"; American Journal of Hematology; Wiley-Liss, Inc.; 2005; pp. 225-231.

* cited by examiner

*Primary Examiner* — Sudhakar Katakam
*Assistant Examiner* — Zachary J Miknis
(74) *Attorney, Agent, or Firm* — BakerHostetler

(57) ABSTRACT

The present invention relates to a pharmaceutical composition/formulation for use in treatment of Iron Deficiency Anaemia (IDA), Anaemia of Inflammation (AOI) and neurodegenerative disorders. More particularly, the invention relates to a pharmaceutical composition/formulation comprising a synergistic combination of Lactoferrin and Guanosine Nucleotides or a pharmaceutically acceptable salt thereof. The application also provides various formulations and methods of preparing the same.

16 Claims, 4 Drawing Sheets

PHARMACEUTICAL COMPOSITION FOR ANAEMIA

CROSS-REFERENCE TO RELATED APPLICATIONS

This application claims priority to International Application No. PCT/IB2019/051706 filed Mar. 4, 2019, which claims to Indian Patent Application No. 201821008809 filed Mar. 9, 2018, all of which are incorporated by reference in their entirety.

FIELD OF THE INVENTION

The present invention relates to a pharmaceutical composition/formulation for use in treatment of Iron Deficiency Anaemia (IDA), Anaemia of Inflammation (AOI) and neurodegenerative disorders. More particularly, the invention relates to a pharmaceutical composition/formulation comprising a synergistic combination of Lactoferrin (LF) and one or more natural Guanosine Nucleotide or a pharmaceutically acceptable salt thereof. The invention also provides various formulations and methods of preparing the same.

BACKGROUND OF THE INVENTION

Anaemia is usually referred to a condition wherein the total amount of red blood cells or hemoglobin in the blood is decreased. Anaemia caused by lack of iron is known as Iron-deficiency anaemia (IDA). IDA relates to a condition when the body doesn't have enough iron to produce adequate amounts of hemoglobin. In such conditions, the blood is unable to carry enough oxygen to the tissues throughout the body and circulation. This anaemia is usually caused by blood loss, insufficient dietary intake and/or poor absorption of iron from food itself. Instances of severe blood loss can include heavy bleeding during menstruation, during childbirth, uterine fibroids, stomach ulcers, colon cancer, and urinary tract bleeding etc. Apart from these conditions, poor absorption of iron may occur due to result of conditions such as Crohn's disease or a gastric bypass.

It is very common that IDA develops during pregnancy either due to lack of iron absorption or due to hormonal changes. The reason behind the deficiency can be attributed to body changes during pregnancy to look after the rising child. It is also essential that women make more blood when they become pregnant. While average woman will have about five litres of blood when not pregnant, they need seven to eight litres of blood as she gets near the term. Consequently, making extra blood cells requires plenty of iron, vitamin B12 and folate to make all of the extra hemoglobin needed. Unfortunately, iron is hard to absorb and difficult to form hemoglobin. Therefore, many women become anemic during pregnancy and require additional iron supplements.

A survey revealed that IDA affected about 1.48 billion people in 2015. A lack of dietary iron is estimated to cause approximately half of all anaemia cases globally. Women and young children are most commonly affected. In 2015 anaemia due to iron deficiency resulted in about 54,000 deaths—down from 213,000 deaths in 1990. Infants and children born to obese women are more likely to develop chronic health conditions such as asthma and diabetes. Hepcidin, a regulator of iron homeostasis, has been shown to be over-expressed in obesity and to correlate with low iron status in the obese persons. Iron reaches the foetus through active transport in the placenta, and hepcidin is known to be one regulator of this process. Further, obesity leads to chronic overexpression of hepcidin as a downstream effect of low-grade chronic inflammation. Specifically, obesity leads to increased interleukin (IL)-6 and IL-1 levels, which up-regulate hepcidin. Similarly, maternal obesity is associated with impaired iron transfer to the foetus. This is due to the effects of a chronic pro-inflammatory environment and increased levels of hepcidin.

During pregnancy, hypoferremia and IDA represent a risk factor for maternal and infant health. In both industrialized and developing countries, hypoferremia and IDA in pregnancy is highly prevalent due to increased iron requirement, enhanced blood volume, and development of the fetal-placenta unit (see, e.g., Umbreit, Am. J. Hematol. 78:225-31 (2005); School, Am. J. Clin. Nutr. 81: 1218-22 (2005)). In addition to enhanced maternal risks, pregnancy-associated anemia results in preterm delivery, retardation of fetal growth, low birth weight, and inferior neonatal health. It is estimated that 41.8% of pregnant women worldwide are anemic and at least half of this anaemia burden is assumed to be due to iron deficiency.

Accordingly, there exists a need for safe and effective therapies for pregnant women to combat iron requirement as well as to prevent or treat hypoferremia and IDA. This is also essentially required to reduce the mortality rate due to such deficiencies.

In general, humans have a daily requirement of ~25 mg of iron, nearly 80% of which is used in erythropoiesis process. A small fraction of this iron is provided by dietary absorption (~1 2 mg), while the majority is provided by recycling iron from senescent erythrocytes via macrophages in liver, spleen and bone marrow. Accordingly, the circulating pool of iron contains only ~10% (~3 mg) of the daily requirement for erythropoiesis, and therefore must be turned over every 2-3 h. Iron recycling is primarily performed by reticuloendothelial macrophages which phagocytize senescent RBCs and then export iron via ferroportin (FPN) back into the circulating pool of Tf-bound iron. Excess iron is also stored within hepatocytes. Hepcidin regulates systemic iron balance by inducing ferroportin degradation to inhibit iron absorption from the duodenum and iron release from macrophage and hepatocyte stores.

During pregnancy average requirements are: basal iron (280 mg), expansion of red cell mass (570 mg), transfer to fetus (200-350 mg), for placenta (50-150 mg), blood loss at delivery (100-250 mg). After deducting iron conserved by amenorrhoea (240-480 mg), an additional 500-600 mg is required in pregnancy or 4-6 mg/day of absorbed iron. As absorption is less than 10% (3-4% in low bio-availability diets), for a minimum of 4-6 mg absorption, at least 40-60 mg of iron should be available in the diet. Since diet alone cannot fulfil the requirement, it is essential to combat the requirement with the additional iron supplements.

Iron homeostasis is tightly regulated through iron absorption, storage and transport. Iron absorption occurs in the proximal duodenum and includes in the apical site of enterocytes the reduction of ferric ions by a ferrireductase (duodenal cytochrome B, DCYTB), the apical uptake and the trans-cellular trafficking via divalent metal transporter 1 (DMT1), the storage into ferritin and finally, the basolateral efflux by the iron transporter ferroportin. Ferroportin, the only known cellular iron exporter from tissues into blood, has been found in all cell types involved in iron export, including enterocytes, hepatocytes, placental cells and macrophages which recycle 20 mg of iron daily from lysed erythrocytes for erythropoiesis.

Another important component of systemic iron homeostasis is hepcidin, a circulating peptide hormone synthesized by hepatocytes in iron loading conditions and secreted in plasma and urine. Hepcidin regulates the entry of iron into plasma through ferroportin. Binding of hepcidin with ferroportin causes the formation of a hepcidin-ferroportin complex resulting in ferroportin phosphorylation, internalization and degradation in lysosomes. Consequently, iron export is hindered and cytosolic iron storage in ferritin is enhanced. Iron homeostasis disorders appear to arise from hepcidin and/or ferroportin dysregulation. It is well known that iron loading and Interleukin-6 (II-6) increase hepcidin gene transcription in hepatocytes.

Patients with chronic infections such as chronic inflammatory disorders, and cancers usually have "anaemia of chronic disease/Inflammation" (ACD/AOI). As inflammation increases interleukin-6 production and consequently increase in hepcidin blocks the macrophage iron release as well as intestinal absorption of iron, resulting in iron dysregulation with hypoferremia and anaemia related to inflammatory disease. Further, obesity can also be considered a chronic inflammatory state that can cause hyposideremia. Patients having anaemia in chronic kidney disease (CKD), is mainly due to the lack of erythropoietin (EPO—indirectly influences iron homeostasis). Since, kidney function (i.e., excretion) plays an important role in hepcidin clearance, concurrently, kidney dysfunction results in decreased hepcidin clearance and consequent hepcidin storage leads to development of hyposideremic anaemia.

Hepcidin level also increases along with the CKD regardless of the inflammatory state. Hemochromatosis can be characterized by low hepcidin production, which increases intestinal absorption of iron and iron release by macrophages which inevitably leads to progressive iron storage in tissues. In chronic diseases, high hepcidin production inhibits iron release from macrophages and intestinal absorption of iron which consequently induces an anemic condition.

Existing Treatment & Disadvantages:

Oral Iron supplements are available commercially either in rapid release dosage forms and/or in controlled release dosage forms.

Rapid release iron supplement dosage forms typically contain a "rapidly dissolving" iron salt which are significantly more soluble in water and gastrointestinal fluids than other salts and metallic forms of iron. Administration of rapid release iron supplement dosage forms can cause excessively high maximum (max) blood-iron concentrations (C), i.e., $C_{max}$, within a short period of time (T) between administration and attainment of $C_{max}$, i.e., $T_{max}$. Accordingly, rapid release iron supplement formulations can cause unpleasant, harmful, or even fatal side effects. Such side effects may include stomach irritation, constipation, and iron poisoning.

Further, the absorption of iron supplements from the gastrointestinal tract is reduced in the presence of divalent non-iron mineral supplements such as magnesium and calcium. Although a wide range of iron compounds is marketed for the treatment of iron deficiency, the results thereof, and the prophylaxis of such iron-deficiency states, the level of iron uptake by the body from these compounds is often quite low, necessitating the administration of relatively high dosage levels of the compound. The administration of a high dose of poorly absorbed iron complexes may cause siderosis of the gut wall and a variety of side effects such as nausea, vomiting, constipation, diarrhoea, abdominal discomfort, shortness of breath, weight loss, headaches, dizziness, anorexia, fatigue, darkened urine, heartburn, darkened teeth, darkened stool, and heavy malodorous stools.

Controlled release iron supplement dosage forms were developed in an attempt to reduce side effects such as those noted above, commonly associated with known iron supplementation therapies. Controlled release iron supplement dosage forms commonly use an iron (II) salt encapsulated in or mixed with a release rate modifying matrix, an iron (III) salt, carbonyl iron or other metallic iron of naturally poor solubility, crystalline iron oxide, iron salt or carbonyl iron complexes with a release rate modifying protein, amino acid, organic acid, natural polymer, anionic complexing agent or synthetic polymer. Iron supplements designed to provide "sustained delivery" of iron have been associated with unpleasant tastes and odors, nausea, stomach irritation and gas formation.

Parenteral iron is required for those not tolerating oral iron or who need rapid correction of anaemia (severe anaemia in last month of pregnancy) and where oral therapy has failed. Parenteral iron can be administered intramuscular (IM) or intravenous (IV). The main drawbacks of IM route are pain, staining of skin, myalgia, arthralgia and injection abscess. Intravenous iron can be administered as total dose infusion; however, utmost caution is needed as anaphylaxis can occur. Iron dextran and iron polymaltose preparations can be used by both IM and IV routes. Two newer IV preparations—iron sucrose and ferric gluconate are associated with reduced side-effects. However, it is a costly alternative and is not necessarily favored by all patients.

Several references disclose that hepcidin levels increased in response to iron therapy regardless of administering oral iron supplement for long term therapy. This increased level of hepcidin is directly associated with decreased iron absorption of subsequent daily iron doses or twice-daily iron doses. The traditional treatments i.e. oral iron therapy and blood transfusion involve significant drawbacks. Oral iron is frequently restricted by limited absorption, low tolerability, non-compliance and side effects.

Even an Intravenous (IV) iron supplementation therapy will also increase hepcidin levels which could adversely affect long-term iron mobilization. I.V. iron could promote cytotoxicity and tissue injury; exacerbate oxidative stress and thus endothelial dysfunction, as well as inflammation and the progression of both CKD and cardiovascular disease. Therefore, it is necessary to regulate hepcidin level which would maintain Iron Homeostasis which in no manner can be achieved by Oral or I.V. Iron Supplement.

In view of the aforementioned drawbacks and side-effects related with the conventional formulations of the iron supplements, it is desired to develop a formulation with natural ingredients which not only will reduce the side effects caused by the iron supplements but will also maintain Iron homeostasis by hepcidin regulation and hence will provide a natural treatment for Iron deficiency anaemia (ADI) and Anaemia of Inflammation (AOI). Additionally, it is also desirable to have a composition/formulation which should be cost-effective and favourable to all age-group patients.

Lactoferrin (LF), also known as lactotransferrin (LTF), is a multifunctional protein of the transferrin family. LF is a globular glycoprotein with a molecular mass of about 80 kDa widely represented in various secretory fluids, such as milk, saliva, tears, and nasal secretions. It is also present in the milk of humans and other mammals, in the blood plasma and neutrophils and is one of the major proteins of virtually all exocrine secretions of mammals. LF can be purified from milk or produced recombinantly. Human colostrum ("first milk") has the highest concentration (7 g/L); followed by human milk (1 g/L), then cow milk (150 mg/L). LF is one of the transferrin proteins that transfer iron to the cells and control the level of free iron in the blood and external secretions. LF belongs to the innate immune system and apart from its main biological function, namely binding and transport of iron ions. It is also known to have antibacterial, antiviral, anti-parasitic, catalytic, anti-cancer, and anti-allergic functions and properties.

LF has been demonstrated to reduce both IL-6 levels and independently reduce hepcidin gene expression. Its antibacterial properties have also been demonstrated to down-regulate the over-expression of macrophages resulting into reduced inflammation and up-regulation of ferroportin expression. Moreover, compared to oral iron supplements, administration of LF has also shown to demonstrate no or minimal side effects such as gastrointestinal irritation, nausea, vomiting, constipation, darkened urine, darkened stool, etc.

Lactoferrin is present in either iron-free (i.e., apo-type) or iron-saturated state (i.e., holo-type) depending on whether it binds irons, which in turn determines the biological properties of lactoferrin. The apo-type lactoferrin is present in normal human milk. Bovine lactoferrin is bovine milk extracted from the form of a basic protein having a variety of biologically active components to develop the protein value.

Further, iron plays an essential role in maintaining various biological functions in all living organisms. Iron affects synthesis and signalling of the neurotransmitters dopamine, noradrenalin, adrenaline and 5-hydroxytryptamine, which are involved in emotion, attention, reward, movement and various other functions. A new approach to manage neurodegenerative disorders can be achieved by iron homeostasis. The present therapies mainly serve as a band-aid therapy, rather than working on the major cause of such neurodegenerative disease which is dysregulation of iron homeostasis. Reduction in IL-6 levels and reduction in Hepcidin gene expression are the two important aspects that are responsible for iron movement in and out of the cells. Thus there is a need to develop formulations for maintaining iron homeostasis by hepcidin regulation and hence provide a natural treatment for the neuro degenerative disorder.

Nucleotides are small molecules composed of three parts, a nitrogenous base, a sugar and one or more phosphates. Nucleotides play many roles in cells. They are the precursors for the nucleic acids. ATP, a nucleotide, is the primary energy currency in a cell. Nucleotides are also used as regulatory molecules. Guanosine is a purine nucleoside comprising guanine attached to ribofuranose, a ribose ring via a β-N-glycosidic bond. Guanosine after phosphorylation turns in to Guanosine monophosphate (GIP), Guanosine diphosphate (GDP), and Guanosine triphosphate (GTP). These functional components play important roles in various biochemical processes for synthesis of nucleic acids and proteins, photosynthesis, muscle contraction and intracellular signal transduction. Amongst them, GMP, also known as 5'-guanidylic acid or guanylic acid (conjugate base guanylate), is a nucleotide that is used as a monomer in RNA. It is an ester of phosphoric acid with the nucleoside guanosine. It consists of the phosphate group, the pentose sugar ribose, and the nucleobase guanine and hence it is a ribonucleoside monophosphate. GMP is commercially produced by microbial fermentation. GDP is a nucleoside diphosphate which is an ester of pyrophosphoric acid with the nucleoside guanosine. GDP consists of a pyrophosphate group, a pentose sugar ribose and the nucleobase guanine. GTP is a purine nucleoside triphosphate which is one of the important blocks required for the synthesis of RNA during the transcription. It has also the role of a source of energy as an activator of substrates in metabolic reactions and used as a source of energy for protein synthesis and gluconeogenesis.

Studies have indicated that guanosine nucleotides may result into— a. Stable binding with hepcidin, preventing hepcidin induced FPN internalization with effective cellular iron efflux.
b. Increased expression of DMT1 and TFR1 (Transferrin receptor) indicating effective iron distribution and decreased ferritin level in the enterocyte, thus preventing increased iron absorption in the cells.
c. Stabilization of Ferroportin in itself resulting in higher effectiveness of iron efflux.

Related Prior Arts

WO 2011/019641 A2 discloses Nutritional compositions and methods of making and using the nutritional compositions wherein the said nutritional compositions comprise one or more exogenous nucleotides selected from the group consisting of 5'-Adenosine Monophosphate, 5'-Guanosine Monophosphate, 5'-Cytosine Monophosphate, 5'-Uracil Monophosphate, 5'-Inosine Monophosphate or 5'-Thymine Monophosphate. The nutritional compositions further comprise at least one prebiotic, at least one probiotic, at least one symbiotic, at least one amino acid, at least one fish oil; at least one phytonutrient; at least one antioxidant; at least one transforming growth factor-beta; or Lactoferrin; or combinations thereof. The said nutritional composition can be in an administrable form such as pharmaceutical formulations, nutritional formulations, dietary supplements, functional foods, beverage products or a combination thereof. The nutritional composition can include the exogenous nucleotides in an amount to be administered ranging from about 0.1 mg/day to about 5.0-6.0 grams/day, including all number, whole or fractions.

WO 2018/009647 A1 discloses a nutritional formula in the form of powder or liquid comprising alpha-lactalbumin enriched whey protein concentrate; beta-casein enriched milk protein; mildly hydrolyzed milk protein; osteopontin; lactoferrin; oleic acid-palmitic acid-oleic acid triglyceride, wherein palmitic acid is at the SN-2 position of the glycerol backbone of the triglyceride; lactose, wherein the lactose is reduced lactose; lutein; docosahexanoic acid; arachidonic acid; galactooligosaccharides; and polydextrose. The nutritional formula of the said invention provides a subject with nutrients similar to those provided by human breast milk.

US 2002/0022052 A1 discloses substantially water free compositions for transdermal or trans epithelial delivery comprising at least one biologically active agent and a pharmaceutically acceptable carrier wherein the biologically active agent is induced into the skin by massage and includes a plurality of fine solid particles sized less than 2 microns dispersed through said carrier. Further, the compositions covered in the said application are in the form of ointment or cream.

WO2007022537A2 discloses the method of treating a disease or condition, such as Anaemia, by administering a chemotactic modulator composition wherein the chemotactic modulator can be selected from the group consisting of Lactoferrin or cGMP. The composition can be administered topically, orally or parenterally and can be in the form of topical gel, a solution, or a tablet. However, there still exists a need for a formulation which supports nutritional requirement along with maintaining iron homeostasis.

From the above disclosure and identified prior arts, it is clear that though options exist for disorders associated with iron deficiency however, many such treatment options are associated with unpleasant or harmful side effects. Therefore, there is still a need for a nutritional or dietary iron supplement that effectively prevents, stabilizes, reverses and/or treats disorders related to iron deficiency along with subsiding all harmful side effects.

Accordingly, there is a further need to formulate a composition/formulation comprising natural ingredients which will reduce ferritin bind iron stores, increase iron efflux in systemic circulation, improve Ferroportin stabilization, decreased Hepcidin and IL-6 levels, reduce inflammatory pathways further affecting hepcidin-Fpn balance and also act as a natural treatment to iron deficiency anaemia (IDA) and anaemia of inflammation (AOI) without any side effects of iron administration by maintaining perfect iron homeostasis with hepcidin regulation.

It has been found that this may be achieved through the administration of a stable composition/formulation comprising combination of Lactoferrin with Guanosine Nucleotides or a pharmaceutically acceptable salt thereof.

SUMMARY OF THE INVENTION

The present application provides a pharmaceutical composition/formulation for use in treatment of Iron Deficiency Anaemia (IDA) and Anaemia of Inflammation (AOI).

The pharmaceutical composition/formulation of the present invention can also be used in the treatment for Neuro-Degenerative Disorders.

The Lactoferrin combination of the present invention is able to provide a safe pharmaceutical composition/formulation with enhanced and/or synergistic effects compared to Lactoferrin alone in the treatment or prevention of IDA or AOI.

The present application provides a pharmaceutical composition/formulation comprising a synergistic combination of Lactoferrin and one or more natural Guanosine Nucleotide or a pharmaceutically acceptable salt thereof.

In a preferred aspect, the present invention provides a pharmaceutical composition/formulation for use in treatment of IDA and AOI, wherein said composition/formulation comprises a synergistic combination of Lactoferrin, one or more natural Guanosine Nucleotide or a pharmaceutically acceptable salt thereof along with pharmaceutically acceptable excipient(s).

In a further preferred aspect, the pharmaceutical composition/formulation of the present invention additionally comprises elemental iron, vitamin C (ascorbic acid), vitamin A (beta carotene), folic acid, folate, vitamin B or a combination thereof.

In another aspect of the present application, a process for the preparation of composition/formulation is described. The process for preparation of the composition comprises:
(a) individually weighing all the ingredients in separate containers,
(b) sifting previously weighed Lactoferrin, guanosine nucleotide(s) or a pharmaceutically acceptable salt thereof, optionally adding elemental iron, vitamin C, vitamin A, folic acid, folate or vitamin B, diluent and disintegrating agent separately,
(c) mixing contents of step (b).
(d) optionally, preparing binder solution in separate container and adding it to step (c) and sieving the granulated wet mass to obtain granules,
(e) drying the obtained granulates until the level of dryness (LOD) is reduced to between 3.0 to 5.0% w/w,
(f) sifting the semi dried granules through suitable sieve, and
(g) sifting previously weighed lubricant(s) and glidant(s) separately through suitable sieve and adding to step (f) to obtain the composition/formulation.

The process further comprises preparing the seal coating and enteric coating solution for enteric coated tablets, film coating solution for film coated tablets and filling and scaling for the capsule dosage forms.

Preferably the composition of this invention is formulated as a composition for an oral formulation and is made into an enteric-coated dosage form.

Lactoferrin breaks down into several large fragments by the gastric digestive enzyme, pepsin, but in case of direct intra-duodenal administration it may reach intestine and exist there for a few hours. However, only the intact native Lactoferrin may reach the gut-associated lymphoid tissue (GALT) and enter the lymphatic system, which is necessary for efficacy. The bioavailability of Lactoferrin is limited as it is susceptible to digestive enzymes in gastrointestinal tract. In this regard, there is a high demand for an appropriate Lactoferrin delivery system that should protect Lactoferrin from digestion in stomach and facilitate its permeability across intestinal epithelium. Specifically, in the composition containing Lactoferrin, which acts on the mucosa of the intestinal tract and is highly sensitive to pepsin, it is technologically meaningful to make the composition into an enteric-coated dosage form. Thus, in order to obtain a stable, safe and effective Lactoferrin formulation in which the pharmacological action as well as efficacy is maintained, it is preferable to make the composition into an enteric coated dosage form.

In adults, orally administered Lactoferrin is prone to the peptic digestion in the stomach. Therefore, an enteric coated LF tablet has been developed for the delivery of an intact molecule of the LF onto the receptor in the intestine. Thus, in such formulation, LF molecules are protected from the proteolytic digestion in the stomach as the tablet is coated by an acid-resistant material, which dissolves easily in a neutral pH condition in the intestine. The enteric-coated LF also known to improve visceral fat-type obesity related for the metabolic syndrome in some studies.

The formulations of the present invention are coated with enteric coated material, which dissolves easily under the neutral pH conditions in the intestine and provide desired pharmacological action.

DETAILED DESCRIPTION OF THE INVENTION

Figure 1:
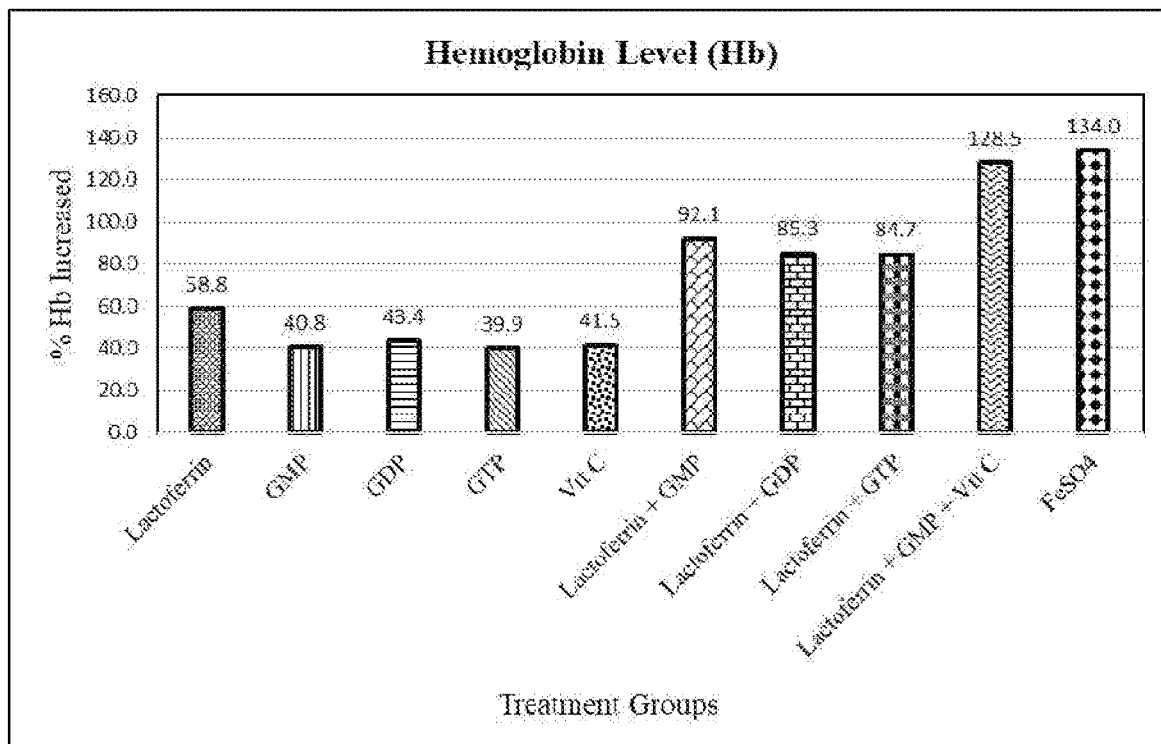
FIG. 1: Effect of test composition/formulation on Hemoglobin level compared to disease control.

While the invention has been described and illustrated with reference to certain embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected along with the present pharmaceutical carriers. Further, the responses may vary depending upon the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

The present invention is directed to a pharmaceutical composition/formulation comprising a synergistic combination of Lactoferrin and one or more natural Guanosine Nucleotide or a pharmaceutically acceptable salt thereof for treatment of Iron Deficiency Anaemia (IDA) and Anaemia of inflammation (AOI). In this regard, the inventors carried out an extensive research studies along with pre-clinical studies and found that the combination of Lactoferrin and one or more natural Guanosine Nucleotide or a pharmaceutically acceptable salt thereof provides synergistic effect for treatment of IDA and AOL.

The pharmaceutical composition/formulation of the present invention can also be used in the treatment for Neuro-Degenerative Disorders.

An objective of the present invention is to provide a pharmaceutical composition/formulation comprising a synergistic combination of Lactoferrin and one or more natural Guanosine Nucleotide or a pharmaceutically acceptable salt thereof.

In one aspect, the pharmaceutical composition/formulation of the present invention may optionally comprise elemental iron, vitamin C, vitamin A, folic acid, folate, vitamin B or a combination thereof.

The Lactoferrin combination of the present invention is able to provide a safe pharmaceutical composition/formulation of Lactoferrin with one or more natural Guanosine Nucleotide or a pharmaceutically acceptable salt thereof with enhanced and/or synergistic effects compared to Lactoferrin alone in the treatment or prevention of IDA or AOL In a preferred aspect, the ratio of Lactoferrin:Natural Guanosine Nucleotide(s) or a pharmaceutically acceptable salt thereof is in a range of 9.1-98.7:1.3-90.9. In a more preferred aspect, the ratio of Lactoferrin:natural Guanosine Nucleotide or a pharmaceutically acceptable salt thereof is 90.91:9.09.

Another objective of the present invention is to provide a synergistic combination of Lactoferrin along with natural Guanosine Nucleotide or a pharmaceutically acceptable salt thereof and optionally including active ingredients selected from elemental iron, vitamin C, vitamin A, folic acid, folate, vitamin B or a combination thereof.

The pharmaceutical composition/formulation of the present invention helps to increase Hemoglobin, Hematocrit % (HCT %) and serum Iron level.

The pharmaceutical composition/formulation of the present invention also helps to reduce Serum Ferritin, Hepcidin and IL-6 level and improve ferroportin stabilization. This hepcidin regulation leads to reduce ferritin bind iron stores, increase iron efflux in systemic circulation and improve Ferroportin stabilization.

Thus, the pharmaceutical composition/formulation of the present invention helps to maintain iron homeostasis in the condition of IDA and AOI without any side effects.

In an embodiment, the pharmaceutical composition/formulation of the present invention comprises Lactoferrin, wherein the amount of Lactoferrin ranges from 5% by wt. to 90% by wt. of the composition/formulation. In an embodiment, the amount of Lactoferrin ranges from 10 to 90% by wt. In another embodiment, the amount of Lactoferrin ranges from 20 to 90% by wt. In yet another embodiment, the amount of Lactoferrin ranges from 30 to 90% by wt. In further embodiment, the amount of Lactoferrin ranges from 40 to 90% by wt. In yet another embodiment, the amount of Lactoferrin ranges from 50 to 90% by wt. In further embodiment, the amount of Lactoferrin ranges from 60 to 90% by wt. In yet another embodiment, the amount of Lactoferrin ranges from 70 to 90% by wt. In further embodiment, the amount of Lactoferrin ranges from 80 to 90% by wt.

In another embodiment, the pharmaceutical composition/formulation of the present invention comprises Lactoferrin, wherein the amount of Lactoferrin in the composition/formulation ranges from 25 mg to 750 mg per unit dose.

Lactoferrin (LF) is present in either iron-free (i.e., apo-type) or partially saturated iron (i.e., native or bovine) or iron-saturated state (i.e., holo-type) depending on whether it binds irons, which in turn determines the biological properties of Lactoferrin.

In a preferred embodiment, the pharmaceutical composition/formulation of the present invention further comprises at least one natural Guanosine Nucleotides or a pharmaceutically acceptable salt thereof wherein the natural Guanosine Nucleotides are selected from GMP, GDP, GTP or the like. The amount of Guanosine Nucleotides or a pharmaceutically acceptable salt thereof that can be used in the composition/formulation of the present invention ranges from 1.0% by wt. to 75% by wt. of the composition/formulation. In an embodiment, the amount of Guanosine Nucleotides or a pharmaceutically acceptable salt thereof ranges from 5 to 75% by wt. In yet another embodiment, the amount of Guanosine Nucleotides or a pharmaceutically acceptable salt thereof ranges from 10 to 75% by wt. In further embodiment, the amount of Guanosine Nucleotides or a pharmaceutically acceptable salt thereof ranges from 20 to 75% by wt. In yet another embodiment, the amount of Guanosine Nucleotides or a pharmaceutically acceptable salt thereof ranges from 30 to 75% by wt. In further embodiment, the amount of Guanosine Nucleotides or a pharmaceutically acceptable salt thereof ranges from 40 to 75% by wt. In yet another embodiment, the amount of Guanosine Nucleotides or a pharmaceutically acceptable salt thereof ranges from 50 to 75% by wt. In further embodiment, the amount of Guanosine Nucleotides or a pharmaceutically acceptable salt thereof ranges from 60 to 75% by wt. In yet another embodiment, the amount of Guanosine Nucleotides or a pharmaceutically acceptable salt thereof ranges from 70 to 75% by wt.

In a preferred embodiment, the amount of Guanosine Nucleotides or a pharmaceutically acceptable salt thereof that can be used in the pharmaceutical composition/formulation of the present invention ranges from 0.25 mg to 1000 mg per unit dose. A pharmaceutically acceptable salt suitable for the invention may be selected from a hydrochloride, a sulfate, a phosphate, acetate, lactate, citrate, a pantothenate, an ascorbate, a succinate, maleate, fumarate, gluconate, a magnesium salt, potassium, sodium, zinc, and the salts of diethanolamine or a combination thereof.

In preferred aspect, the pharmaceutical composition/formulation of the present invention comprises a synergistic combination of Lactoferrin, Disodium GMP and pharmaceutically acceptable excipients.

In an embodiment, the pharmaceutical composition/formulation of the present invention optionally comprises other active ingredients such as Iron.

The, pharmaceutical composition/formulation of the present invention may include iron as physiologically acceptable grades of elemental iron that can be used in a single dosage form composition of the disclosure and include without limitation elemental iron, iron compounds in the form of a salt (soluble, slightly soluble, or insoluble), chelated iron (specifically, chelated to an amino acid), iron complexes, non-reactive iron such as carbonyl iron and reduced iron, and combinations thereof.

Non-limiting examples of suitable soluble iron salts include ferric hypophosphite, ferric albuminate, ferric chloride, ferric citrate, ferric oxide saccharate, ferric ammonium citrate, ferrous chloride, ferrous gluconate, ferrous iodide, ferrous sulfate, ferrous lactate, ferrous fumarate, heme, ferric trisglycinate, ferrous bisglycinate, ferrous asparto glycinate, ferric nitrate, ferrous hydroxide saccharate, ferric sulfate, ferric gluconate, ferric aspartate, ferrous sulfate heptahydrate, ferrous phosphate, ferric ascorbate, ferrous formate, ferrous acetate, ferrous malate, ferrous glutamate, ferroglycine sulfate, ferric oxide hydrate, ferric pyrophosphate soluble, ferric hydroxide saccharate, ferric manganese saccharate, ferric subsulfate, ferric ammonium sulfate, ferrous ammonium sulfate, ferric sesquichloride, ferric manganese citrate, ferric quinine citrate, ferric sodium citrate, ferric sodium edetate, ferric formate, ferric ammonium oxalate, ferric potassium oxalate, ferric sodium oxalate, ferric peptonate, ferric manganese peptonate, other pharmaceutically acceptable iron salts, and combinations thereof.

Non-limiting examples of suitable slightly soluble iron salts include ferric acetate, ferric fluoride, ferric phosphate, ferric pyrophosphate, ferrous pyrophosphate, ferrous carbonate saccharated, ferrous carbonate mass, ferrous succinate, ferrous citrate, ferrous tartrate, ferric fumarate, ferric succinate, ferrous hydroxide, ferrous nitrate, ferrous carbonate, ferric sodium pyrophosphate, ferric tartrate, ferric potassium tartrate, ferric subcarbonate, ferric glycerophosphate, ferric saccharate, ferric hydroxide saccharate, ferric manganese saccharate, ferrous ammonium sulfate, other pharmaceutically acceptable iron salts, and combinations thereof.

Non-limiting examples of suitable insoluble iron salts include ferric sodium pyrophosphate, ferrous carbonate, ferric hydroxide, ferrous oxide, ferric oxyhydroxide, ferrous oxalate, other pharmaceutically acceptable iron salts and combinations thereof.

In a specific embodiment, iron may be included in the form of ferrous bisglycinate or other salt form. In another specific embodiment, iron may be included in the form of ferric pyrophosphate.

The amount of Elemental Iron that can be used in the pharmaceutical composition/formulation of the present invention ranges from 30% by wt. to 45% by wt. of the composition/formulation.

In the preferable embodiment, the amount of Elemental Iron that can be used in the pharmaceutical composition/formulation of the present invention ranges from 30 mg to 500 mg per unit dose.

In another preferred aspect, the pharmaceutical composition/formulation of the present invention comprises a synergistic combination of Lactoferrin, Guanosine Nucleotides or a pharmaceutically acceptable salt thereof, Elemental Iron and pharmaceutically acceptable excipients.

More preferably, the pharmaceutical composition/formulation of the present invention comprises a synergistic combination of Lactoferrin, Disodium GMP, Ferrous bis-glycinate and pharmaceutically acceptable excipients. In an embodiment, the pharmaceutical composition/formulation of the present invention optionally comprise other natural active ingredients such as Vitamin C (Ascorbic Acid), Vitamin A (Beta carotene), and Folic Acid, Folate, Vitamin B (Vitamin $B_{12}$/Cobalamin) or the like.

In a preferred embodiment, the amount of Vitamin C that can be used in the pharmaceutical composition/formulation of the present invention ranges from 5% by wt. to 65% by wt. of the composition/formulation.

In a preferable embodiment the amount of Vitamin C that can be used in the pharmaceutical composition/formulation of the present invention ranges from 20 mg to 4000 mg per unit dose.

In another preferred aspect, the pharmaceutical composition/formulation of the present invention comprises a synergistic combination of Lactoferrin, Guanosine Nucleotides or a pharmaceutically acceptable salt thereof, Vitamins and pharmaceutically acceptable excipients.

More preferably, the pharmaceutical composition/formulation of the present invention comprises a synergistic combination of Lactoferrin, Disodium GMP, vitamin C and pharmaceutically acceptable excipients.

In a preferred embodiment, the amount of Vitamin A that can be used in the pharmaceutical composition/formulation of the present invention ranges from 0.5% by wt. to 3% by wt. of the composition/formulation.

In a preferred embodiment, the amount of Vitamin A that can be used in the pharmaceutical composition/formulation of the present invention ranges from 450 mcg to 10,000 mcg per unit dose.

In a preferred embodiment, the amount of Folic Acid or Folate that can be used in the pharmaceutical composition/formulation of the present invention ranges from 0.05% by wt. to 0.75% by wt. of the composition/formulation.

In a preferred embodiment, the amount of Folic Acid or Folate that can be used in the pharmaceutical composition/formulation of the present invention ranges from 6 mcg to 5000 mcg per unit dose.

In another preferred aspect, the pharmaceutical composition/formulation of the present invention comprises a synergistic combination of Lactoferrin, Guanosine Nucleotides or a pharmaceutically acceptable salt thereof, Elemental Iron, folic acid and pharmaceutically acceptable excipients.

More preferably, the pharmaceutical composition/formulation of the present invention comprises a synergistic combination of Lactoferrin, Disodium GMP, Ferrous bis-glycinate, folic acid and pharmaceutically acceptable excipients.

In a preferred embodiment, the amount of Vitamin B (Vitamin $B_{12}$/Cobalamin) that can be used in the pharmaceutical composition/formulation of the present invention ranges from 1% by wt. to 5% by wt. of the composition/formulation.

In a preferred embodiment, the amount of Vitamin B (Vitamin $B_{12}$/Cobalamin) that can be used in the pharmaceutical composition/formulation of the present invention ranges from 50 mcg to 5000 mcg per unit dose. In another embodiment, the pharmaceutical composition/formulation according to the present invention can be formulated for oral administration. For oral administration, the solid compositions can be, for example, in the form of tablets, capsules, pills, hard capsules filled with liquids or solids, soft capsules, powders, granules, sachets, enteric coated tablet or capsule, modified release tablet or capsule etc. The pharmaceutical composition/formulation may further comprise pharmaceutically acceptable excipients. The preferred excipients are selected from diluent, binder, disintegrant, lubricant, glidant, etc. and combinations thereof.

The diluents are selected from microcrystalline cellulose, lactose (anhydrous/monohydrate/spray dried), starch, cellulose powder, silicified microcrystalline cellulose, ammonium alginate, calcium carbonate, calcium lactate, dibasic calcium phosphate (anhydrous/dibasic dehydrate/tribasic), calcium silicate, calcium sulfate, cellulose acetate, compressible sugar, confectioner's sugar, corn starch, pregelatinized starch, dextrates, dextrin, dextrose, erythritol, ethylcellulose, fructose, fumaric acid, glyceryl palmitostearate, isomalt, kaolin, lactitol, magnesium carbonate, magnesium oxide, maltodextrin, maltose, mannitol, medium-chain triglycerides, polydextrose, polymethacrylates, simethicone, sodium alginate, sodium chloride, sorbitol, sterilizable maize, sucrose, sugar spheres, sulfobutylether β-cyclodextrin, talc tragacanth, trehalose, xylitol or the like. The amount of diluent in the pharmaceutical composition/formulation of the present invention ranges from 5% to 45% by wt. of the composition/formulation.

The binder is selected from Hypromellose, starch, acacia, agar, alginic acid, calcium carbonate, calcium lactate, carbomers, carboxymethylcellulose sodium, carrageenan, cellulose acetate phthalate, ceratonia, chitosan, copovidone, corn starch, pregelatinized starch, cottonseed oil, dextrates, dextrin, dextrose, ethylcellulose, gelatin, glyceryl behenate, guar gum, hydrogenated vegetable oil type I, hydroxyethyl cellulose, hydroxy-ethylmethyl cellulose, hydroxypropyl cellulose, inulin, lactose, liquid glucose, low-substituted Hypromellose, magnesium aluminum silicate, maltodextrin, maltose, methyl-cellulose, microcrystalline cellulose, pectin, poloxamer, polycarbophil, polydextrose, polyethylene oxide, polymethacrylates, povidone, sodium alginate, stearic acid, sucrose, sunflower oil, tricaprylin, vitamin E polyethylene glycol succinate, zein or the like. The amount of binder in the pharmaceutical composition/formulation of the present invention ranges from 1% by wt. to 7% by wt. of the composition/formulation.

The disintegrating agent is selected from croscarmellose sodium, crospovidone, carboxymethyl cellulose (sodium/calcium), sodium starch glycolate, alginic acid, calcium alginate, cellulose, powdered, chitosan, colloidal silicon dioxide, corn starch, docusate sodium, glycine, guar gum, hydroxypropyl cellulose low-substituted, magnesium aluminum silicate, methylcellulose, microcrystalline cellulose, polacrilin potassium, povidone, sodium alginate, pregelatinized starch or the like. The amount of disintegrating agent in the pharmaceutical composition/Formulation of the present invention ranges from 1% to 25% by wt. of the composition/formulation.

The lubricant is selected from magnesium stearate, zinc stearate, calcium stearate, glycerin monostearate, glyceryl behenate, glyceryl palmitostearate, hydrogenated castor oil, hydrogenated vegetable oil type I, light mineral oil, magnesium lauryl sulfate, medium-chain triglycerides, mineral oil, myristic acid, palmitic acid, poloxamer, polyethylene glycol, sodium benzoate, sodium chloride, sodium lauryl sulfate, sodium stearyl fumarate, stearic acid, talc, potassium benzoate or the like. The amount of Lubricant in the pharmaceutical composition/formulation of the present invention ranges from 0.5% to 5% by wt. of the composition/formulation.

The glidant is selected from colloidal silicon dioxide, talc, calcium phosphate tribasic, cellulose powdered, hydrophobic colloidal silica, magnesium oxide, magnesium silicate, magnesium trisilicate, silicon dioxide or the like. The amount of Glidant in the pharmaceutical composition/formulation of the present invention ranges from 0.5% to 5% by wt. of the composition/formulation.

The coating layer for the composition/formulation of the present invention is selected from film coating, seal coating or enteric coating. The total amount of coating agent in the pharmaceutical composition/formulation of the present invention ranges from 1.0% to 15% by wt. of the composition/formulation.

The seal coating agent is selected from Instamoistshield (Hydroxypropyl methyl cellulose, Polyethylene glycol, Talc, Titanium dioxide, Ethyl cellulose), gelatin, copovidone, hydroxyethyl cellulose, ethyl cellulose, starch, vanillin, hydroxypropyl cellulose, guar gum, maleic acid, Hypromellose, polymethacrylates, Methyl cellulose or the like. The amount of seal coating agent in the pharmaceutical composition/formulation of the present invention ranges from 1.0% to 3.0% by wt. of the composition/formulation.

The enteric coating agent is selected from Instacoat EN HPMC P (Hydroxypropyl methyl cellulose Phthalate. Polyethylene glycol, Titanium dioxide, Red Iron oxide), Methacrylate copolymer, shellac, sodium alginate, acetyltributyl citrate, carbomers, cellulose acetate phthalate, guar gum, hypromellose acetate succinate, hypromellose phthalate, polymethacrylates, polyvinyl acetate phthalate, potassium chloride, glycerin, Sureteric, tributyl citrate, triethyl citrate, triolein, white wax, zein, cellulose acetate phthalate with ethyl cellulose, chitosan, hydroxypropyl cellulose, polymethacrylates or the like. The amount of enteric coating agent in the pharmaceutical composition/formulation of the present invention ranges from 5.0% to 10.0% by wt. of the composition/formulation.

The film coating agent is selected from Instacoat Universal (Hydroxypropyl methyl cellulose, Polyethylene glycol, Talc, Titanium dioxide), guar gum, Hypromellose, Povidone, hydroxypropyl cellulose, cellulose acetate, polydextrose, Ethyl cellulose, methylcellulose, gelatin, glycerin, maltodextrin, starch or the like. The amount of film coating agent in the pharmaceutical composition/formulation of the present invention ranges from 2.0% to 3.0% by wt. of the composition/formulation.

The solvent is selected from water, alcohol, isopropyl alcohol, propylene glycol, almond oil, benzyl alcohol, benzyl benzoate, butylene glycol, carbon dioxide, castor oil, corn oil (maize), cottonseed oil, dibutyl phthalate, diethyl phthalate, dimethyl ether, albumin, dimethyl phthalate, dimethyl sulfoxide, dimethylacetamide, ethyl acetate, ethyl lactate, ethyl oleate, glycerin, glycofurol, isopropyl myristate, isopropyl palmitate, light mineral oil, medium-chain triglycerides, methyl lactate, mineral oil, monoethanolamine, octyldodecanol, olive oil, peanut oil, polyethylene glycol, polyoxyl 35 castor oil, propylene carbonate, pyrrolidone, safflower oil, sesame oil, soybean oil, sunflower oil, triacetin, tricaprylin, triethanolamine, triethyl citrate, triolein, water-miscible solvents or the like. The amount of solvent in the pharmaceutical composition/formulation of the present invention is used in a quantity sufficient In a preferred aspect, the present invention provides a pharmaceutical composition/formulation for use in treatment of IDA and AOI, wherein said composition/formulation comprises a synergistic combination of Lactoferrin, natural Guanosine Nucleotide(s) or a pharmaceutically acceptable salt thereof, and optional active ingredients along with pharmaceutically acceptable excipient(s).

The following methods and excipients are merely exemplary and are in no way limiting. In pharmaceutical dosage forms, natural Guanosine Nucleotide(s) employed in the present invention may be used in the form of their pharmaceutically acceptable salts, and also may be used alone or in appropriate association, as well as in combination with other pharmaceutically active compounds.

Some of the exemplary compositions/formulations of the present invention are described below:

| Composition/Formulation 1 | | |
|---|---|---|
| S. No | Ingredients | % w/w |
| 1 | Lactoferrin | 5 to 90 |
| 2 | Guanosine Nucleotide(s) or a pharmaceutically acceptable salt thereof | 1 to 75 |

| Composition/Formulation 2 | | |
|---|---|---|
| S. No | Ingredients | % w/w |
| 1 | Lactoferrin | 5 to 90 |
| 2 | Guanosine Nucleotide(s) or a pharmaceutically acceptable salt thereof | 1 to 75 |
| | Optional ingredient | |
| 3 | Vitamin A | 0.5 to 3 |

| Composition/Formulation 3 | | |
|---|---|---|
| S. No | Ingredients | % w/w |
| 1 | Lactoferrin | 5 to 90 |
| 2 | Guanosine Nucleotide(s) or a pharmaceutically acceptable salt thereof | 1 to 75 |
| | Optional ingredient | |
| 3 | Vitamin B | 1 to 5 |

| Composition/Formulation 4 | | |
|---|---|---|
| S. No | Ingredients | % w/w |
| 1 | Lactoferrin | 5 to 90 |
| 2 | Guanosine Nucleotide(s) or a pharmaceutically acceptable salt thereof | 1 to 75 |
| | Optional ingredient | |
| 3 | Vitamin C | 5 to 65 |

| Composition/Formulation 5 | | |
|---|---|---|
| S. No | Ingredients | % w/w |
| 1 | Lactoferrin | 5 to 90 |
| 2 | Guanosine Nucleotide(s) or a pharmaceutically acceptable salt thereof | 1 to 75 |
| | Optional ingredient | |
| 3 | Folic Acid, Folate | 0.05 to 0.75 |

| Composition/Formulation 6 | | |
|---|---|---|
| S. No | Ingredients | % w/w |
| 1 | Lactoferrin | 5 to 90 |
| 2 | Guanosine Nucleotide(s) or a pharmaceutically acceptable salt thereof | 1 to 75 |
| | Optional ingredients | |
| 3 | Elemental Iron (Ferrous Bisglycinate, Ferric pyrophosphate, Ferrous Fumarate, Ferric citrate, etc.) | 30 to 45 |

| Composition/Formulation 7 | | |
|---|---|---|
| S. No | Ingredients | % w/w |
| 1 | Lactoferrin | 5 to 90 |
| 2 | Guanosine Nucleotide(s) or a pharmaceutically acceptable salt thereof | 1 to 75 |
| | Optional ingredients | |
| 3 | Elemental Iron (Ferrous Bisglycinate, Ferric pyrophosphate, Ferrous Fumarate, Ferric citrate, etc.) | 30 to 45 |
| 4 | Vitamin C | 5 to 65 |
| 5 | Vitamin A | 0.5 to 3 |
| 6 | Folic Acid, Folate | 0.05 to 0.75 |
| 7 | Vitamin B | 1 to 5 |

General Process for Preparation of the Formulations of the Present Invention

Manufacturing Procedure:—

(Tablet Section—Enteric Coated)

The uncoated tablet used as a core for enteric coated formulation in the present invention can be prepared by dry or wet granulation.

Dry Granulation:
1. Weigh accurately all the ingredients in separate containers.
2. Pass previously weighed ingredients (Such as Active Ingredients, diluent, disintegrant) separately through sieve #30.
3. Mix content of step 2 in blender with slow speed.
4. Pass previously weighed glidant and lubricant (such as Magnesium stearate & Colloidal silicon dioxide) through sieve #40. Transfer it to blender & run blender.
5. Compress the blend with medium force with Round biconvex shape B tooling punch.

Wet Granulation:
1. Weigh accurately all the ingredients in separate containers.
2. Pass previously weighed ingredients (Such as Active Ingredients, diluent, disintegrant) separately through sieve #40.
3. Mix content of step 2 in Rapid mixer granulator (RMG) with impeller of slow speed.
4. Binder solution Preparation: In separate container, weigh a binding agent (such as Polyvinyl Pyrrolidone K-30, HPMC 6 cps) and dissolve it in solvent (Such as Isopropyl alcohol, Purified water) to get clear solution
5. Binding: Add binder solution to step 3 in RMG at slow speed of impeller. Check the consistency and binding. If necessary, additional wetting shall be impacted by Solvent.
6. Transfer the granulated wet mass obtained into bowl and carry out drying in a Fluid bed dryer at 50° C.±5° C. till the LOD of the blend comes down to between 3.0 to 5.0% w/w.

7. Pass semi dried granules through sieve #14. Perform the size reduction of the granules which are retaining on sieve #16 using Multimill with 2.5 mm screen.
8. Finally pass the dried granules through sieve #16. Perform the size reduction of the granules which are retaining on sieve #20 using Multimill with 1.5 mm screen.
9. Finally pass the above granules through sieve #24.
10. Pass previously weighed disintegrant and glidant through sieve #40 and mix with Step-9.
11. Pass previously weighed lubricant (such as Magnesium stearate) through sieve #40 and mix with Step-10.
12. Compress the tablets blend with medium compression force round shaped D tooling punch.

Preparation of Seal Coating Solution:

13. Take weighed quantity of Solvent (Such as Isopropyl alcohol) in mixing vessel.
14. Using Mechanical Stirrer, stir the Solvent to form a vortex.
15. Add required quantity of Seal coating agent (Such as InstaMoistSheild) to the center of the solvent vortex in a slow steady stream, avoiding clumping and maintain a vortex, then add required quantity of Solvent (Methylene dichloride).
16. Once entire qty. of Seal coating agent has been added, reduce the stirrer speed to eliminate the vortex. Continue mixing.
17. Filter the solution through #100 nylon cloth and collect the material in S.S Vessels.
18. Transfer tablets in to the coating pan & Connect the peristaltic pump into coating solution vessel. Maintain the temperature and humidity of coating area at 25±2° C. and 50±5%. Perform coating at maximum tablet rolling point as per following parameters:

| Parameter | Limit |
| --- | --- |
| Bed Temperature | 32 ± 2° C. |
| Preheat time | 5 to 10 min |
| Air pressure | 1.0 to 1.5 Kg/cm$^2$ |
| Gun to bed distance | 6 to 10 Inch |

19. Perform the coating till the weight gain of tablet reaches approx. 1.0 to 3.0%.

Preparation of Enteric Coating Solution:

20. Take weighed quantity of Solvent (such as purified water, isopropyl alcohol, methylene dichloride) in mixing vessel.
21. Using Mechanical Stirrer, stir the Solvent (Such as Purified water, Isopropyl alcohol, methylene dichloride and glycerin) to form a vortex.
22. Add required quantity of Enteric coating agent (Such as Instacoat EN HPMC P or mixture of Methylacry-lateco polymer, Shellac, sodium alginate and Talc) to the center of the solvent vortex in a slow steady stream, avoiding clumping and maintain a vortex.
23. Continue mixing for 45 to 60 minutes.
24. Filter the solution through 0.5 mm sieve and collect the material in S.S Vessels.
25. Transfer tablets in to the coating pan & Connect the peristaltic pump into coating solution vessel. Maintain the temperature and humidity of coating area at 25±2° C. and 50±5%. Perform coating at maximum tablet rolling point as per following parameters:

| Parameter | Limit |
| --- | --- |
| Bed Temperature | 30 ± 2° C. |
| Preheat time | 5 to 10 min |
| Air pressure | 1.0 to 1.5 Kg/cm$^2$ |
| Gun to bed distance | 6 to 10 Inch |

26. Perform the coating till the weight gain of tablet reaches approx. 5.0 to 10.0%.

Manufacturing Procedure:—
(Tablet Section—Film Coated)

1. Weigh accurately all the Ingredient in separate containers.
2. Pass previously weighed ingredients (Such as Active Ingredients, diluent, disintegrant, glidant) separately through sieve #310
3. Mix content of step 2 in Blender with slow speed.
4. Pass previously weighed lubricant (such as Magnesium stearate) through sieve #40. Transfer it to blender & run blender.
5. Compress the blend with medium force with Round biconvex shape B tooling punch.

Preparation of Film Coating Solution:

6. Take weighed quantity of Solvent (such as Isopropyl alcohol) in mixing vessel.
7. Using Mechanical Stirrer, stir the Solvent to form a vortex.
8. Add required quantity of Film coating agent (Such as Instacoat Universal) to the center of the solvent vortex in a slow steady stream, avoiding clumping and maintain a vortex stir for 5 minutes, then add quantity of Solvent (such as methylene dichloride).
9. Once entire qty. of Film coating agent has been added, reduce the stirrer speed to eliminate the vortex. Continue mixing.
10. Filter the solution through #100 nylon cloth and collect the material in S.S Vessels.
11. Transfer tablets in to the coating pan & Connect the peristaltic pump into coating solution vessel. Maintain the temperature and humidity of coating area at 25±2° C. and 50±5% respectively. Perform coating at maximum tablet rolling point as per following parameters:

| Parameter | Limit |
| --- | --- |
| Bed Temperature | 32 ± 2° C. |
| Preheat time | 5 to 10 min |
| Air pressure | 1.0 to 1.5 Kg/cm$^2$ |
| Gun to bed distance | 6 to 10 Inch |

12. Perform the coating till the weight gain of tablet reaches approx. 2.0 to 3.0%.

Manufacturing Procedure:—(Capsule Section)

1, Weigh accurately all the Ingredients in separate containers.
2. Pass previously weighed ingredients (Such as Active Ingredients, diluent, disintegrant, glidant) separately through sieve #30.
3. Mix content of step 2 in Blender with slow speed.
4. Pass previously weighed lubricant (such as Magnesium stearate) through sieve #40. Transfer it to blender & run blender.
5. Filling and Sealing the blend with HPMC capsule shells.

6. Transfer the filled capsules into the hopper of polishing and visual inspection machine to remove the debris of powder sticking with the capsule shells.

EXAMPLES

It is understood that the foregoing examples are merely illustrative of the present invention. Certain modifications of the articles and/or methods employed may be made and still achieve the objectives of the invention. Such modifications are contemplated as within the scope of the claimed invention. For Experiments Lactoferrin was obtained from Tatura Milk Industries Limited, 238-240 Hogan Street Tatura 3616 Vic Australia and it's trader in India Vasta Biotech Pvt. Ltd., SVN House, 10 C.P. Ramaswamy Aiyar Road, Alwarpet, Chennai 600 018 and guanosine nucleotides—Disodium GMP, GDP & GTP from Cima Science Wuxi Cima Science Co. Ltd, 3 #Building, No. 288 Shibawan Road Wuxi 214064 Jiangsu China.

Example 1

| S. No | Ingredients | Wt. in mg | % W/W |
|---|---|---|---|
| | Dry Mixing | | |
| 1 | Lactoferrin | 100 | 33.33 |
| 2 | Disodium Guanosine 5-Monophosphate (GMP) | 10 | 3.33 |
| 3 | Microcrystalline cellulose 102 | 109 | 36.33 |
| 4 | Crospovidone | 45 | 15.00 |
| 5 | Croscarmellose sodium | 25 | 8.33 |
| 6 | Magnesium Stearate | 5.5 | 1.83 |
| 7 | Colloidal silicon dioxide | 5.5 | 1.83 |
| Wt. of uncoated tablets | | 300.0 | 100.00 |
| | Seal coating Ingredients | | |
| 8 | InstaMoistshield | 6 | 2.00 |
| 9 | Isopropyl alcohol | QS | Q.S |
| 10 | Methylene dichloride | QS | Q.S |
| | Enteric coating Ingredients | | |
| 11 | Instacoat EN HPMC P | 29 | 9.50 |
| 12 | Isopropyl alcohol | QS | Q.S |
| 13 | Methylene dichloride | QS | Q.S |
| Wt. of Enteric coating | | 35 | 11.50 |
| Wt. of Enteric coated tablets | | 335.0 | — |

Example 2

| S. No | Ingredients | Wt. in mg | % W/W |
|---|---|---|---|
| | Dry Mixing | | |
| 1 | Lactoferrin | 750 | 88.24 |
| 2 | Disodium Guanosine 5-Monophosphate (GMP) | 10 | 1.18 |
| 3 | Microcrystalline cellulose 102 | 64 | 7.53 |
| 4 | Crospovidone | 15 | 1.76 |
| 5 | Magnesium Stearate | 5.5 | 0.65 |
| 6 | Colloidal silicon dioxide | 5.5 | 0.65 |
| Wt. of uncoated tablets | | 850.0 | 100.00 |
| | Seal coating Ingredients | | |
| 7 | InstaMoistshield | 21.2 | 2.50 |
| 8 | Isopropyl alcohol | QS | Q.S |
| 9 | Methylene dichloride | QS | Q.S |
| | Enteric coating Ingredients | | |
| 10 | Instacoat EN HPMC P | 63.8 | 7.33 |
| 11 | Isopropyl alcohol | QS | Q.S |
| 12 | Methylene dichloride | QS | Q.S |
| Wt. of Enteric coating | | 85.0 | 9.83 |
| Wt. of Enteric coated tablets | | 935.0 | — |

Example 3

| S. No | Ingredients | Wt. in mg | % W/W |
|---|---|---|---|
| | Dry Mixing | | |
| 1 | Lactoferrin | 25 | 7.14 |
| 2 | Disodium Guanosine 5-Monophosphate (GMP) | 250 | 71.43 |
| 3 | Microcrystalline cellulose 102 | 49 | 14.00 |
| 4 | Crospovidone | 15 | 4.29 |
| 5 | Magnesium Stearate | 5.5 | 1.57 |
| 6 | Colloidal silicon dioxide | 5.5 | 1.57 |
| Wt. of uncoated tablets | | 350.0 | 100.00 |
| | Seal coating Ingredients | | |
| 7 | InstaMoistshield | 10 | 2.50 |
| 8 | Isopropyl alcohol | QS | Q.S |
| 9 | Methylene dichloride | QS | Q.S |
| | Enteric coating Ingredients | | |
| 10 | Instacoat EN HPMC P | 25 | 8.00 |
| 11 | Isopropyl alcohol | QS | Q.S |
| 12 | Methylene dichloride | QS | Q.S |
| Wt. of Enteric coating | | 35 | 10.50 |
| Wt. of Enteric coated tablets | | 385.0 | — |

Example 4

| S. No | Ingredients | Wt. in mg | % W/W |
|---|---|---|---|
| | Dry Mixing | | |
| 1 | Lactoferrin | 100 | 47.62 |
| 2 | Guanosine Nucleotide diphosphate (GDP) | 10 | 4.76 |
| 3 | Dicalcium phosphate | 74 | 35.24 |
| 4 | Croscarmellose sodium | 15 | 7.14 |
| 5 | Magnesium Stearate | 5.5 | 2.62 |
| 6 | Colloidal silicon dioxide | 5.5 | 2.62 |
| Wt. of uncoated tablets | | 210.0 | 100.0 |
| | Seal coating Ingredients | | |
| 7 | InstaMoistshield | 5.3 | 2.50 |
| 8 | Isopropyl alcohol | QS | Q.S |
| 9 | Methylene dichloride | QS | Q.S |

-continued

| S. No | Ingredients | Wt. in mg | % W/W |
|---|---|---|---|
| Enteric coating Ingredients | | | |
| 10 | Instacoat EN HPMC P | 19.7 | 8.95 |
| 11 | Isopropyl alcohol | QS | Q.S |
| 12 | Methylene dichloride | QS | Q.S |
| Wt. of Enteric coating | | 25 | 11.45 |
| Wt. of Enteric coated tablets | | 235.0 | — |

Example 5

| S. No | Ingredients | Wt. in mg | % W/W |
|---|---|---|---|
| Dry Mixing | | | |
| 1 | Lactoferrin | 100 | 43.48 |
| 2 | Guanosine Nucleotide triphosphate (GTP) | 10 | 4.35 |
| 3 | Lactose Anhydrous | 94 | 40.87 |
| 4 | Sodium starch glycolate | 15 | 6.52 |
| 5 | Magnesium Stearate | 5.5 | 2.39 |
| 6 | Colloidal silicon dioxide | 5.5 | 2.39 |
| Wt. of uncoated tablets | | 230.0 | 100.00 |
| Seal coating Ingredients | | | |
| 7 | InstaMoistshield | 7 | 3.00 |
| 8 | Isopropyl alcohol | QS | Q.S |
| 9 | Methylene dichloride | QS | Q.S |
| Enteric coating Ingredients | | | |
| 10 | Instacoat EN HPMC P | 18 | 7.90 |
| 11 | Isopropyl alcohol | QS | Q.S |
| 12 | Methylene dichloride | QS | Q.S |
| Wt. of Enteric coating | | 25.0 | 10.90 |
| Wt. of Enteric coated tablets | | 255.0 | — |

Example 6

| S. No | Ingredients | Wt. in mg | % W/W |
|---|---|---|---|
| Dry Mixing | | | |
| 1 | Lactoferrin | 100 | 33.33 |
| 2 | Disodium Guanosine 5-Monophosphate (GMP) | 10 | 3.33 |
| 3 | Guanosine Nucleotide triphosphate (GTP) | 80 | 26.67 |
| 4 | Lactose Anhydrous | 84 | 28.00 |
| 4 | Croscarmellose sodium | 15 | 5.00 |
| 6 | Magnesium Stearate | 5.5 | 1.83 |
| 7 | Colloidal silicon dioxide | 5.5 | 1.83 |
| Wt. of Enteric coating | | 300.0 | 100.00 |
| Seal coating Ingredients | | | |
| 8 | InstaMoistshield | 7.5 | 2.50 |
| 9 | Isopropyl alcohol | QS | Q.S |
| 10 | Methylene dichloride | QS | Q.S |

-continued

| S. No | Ingredients | Wt. in mg | % W/W |
|---|---|---|---|
| Enteric coating Ingredients | | | |
| 11 | Instacoat EN HPMC P | 27.5 | 8.95 |
| 12 | Isopropyl alcohol | QS | Q.S |
| 13 | Methylene dichloride | QS | Q.S |
| Wt. of Enteric coating | | 35.0 | 11.45 |
| Wt. of Enteric coated tablets | | 335.0 | — |

Example 7

| S. No | Ingredients | Wt. in mg | % W/W |
|---|---|---|---|
| Dry Mixing | | | |
| 1 | Lactoferrin | 100 | 25.00 |
| 2 | Disodium Guanosine 5-Monophosphate (GMP) | 10 | 2.50 |
| 3 | Guanosine Nucleotide diphosphate (GDP) | 100 | 25.00 |
| 4 | Guanosine Nucleotide triphosphate (GTP) | 80 | 20.00 |
| 5 | Microcrystalline cellulose 102 | 84 | 21.00 |
| 6 | Crospovidone | 15 | 3.75 |
| 7 | Magnesium Stearate | 5.5 | 1.38 |
| 8 | Colloidal silicon dioxide | 5.5 | 1.38 |
| Wt. of uncoated tablets | | 400.0 | 100.00 |
| Seal coating Ingredients | | | |
| 9 | InstaMoistshield | 12 | 3.00 |
| 10 | Isopropyl alcohol | QS | Q.S |
| 11 | Methylene dichloride | QS | Q.S |
| Enteric coating Ingredients | | | |
| 12 | Instacoat EN HPMC P | 33 | 8.03 |
| 13 | Isopropyl alcohol | QS | Q.S |
| 14 | Methylene dichloride | QS | Q.S |
| Wt. of Enteric coating | | 45.0 | 11.03 |
| Wt. of Enteric coated tablets | | 445.0 | — |

Example 8

| S. No | Ingredients | Wt. in mg | % W/W |
|---|---|---|---|
| Dry Mixing | | | |
| 1 | Lactoferrin | 100 | 40.00 |
| 2 | Guanosine Nucleotide diphosphate (GDP) | 10 | 4.00 |
| 3 | Vitamin A | 2.5 | 1.00 |
| 4 | Dicalcium phosphate anhydrous | 102.5 | 41.00 |
| 5 | Sodium starch glycolate | 15 | 6.00 |
| 6 | Magnesium Stearate | 10 | 4.00 |
| 7 | Colloidal silicon dioxide | 10 | 4.00 |
| Wt. of uncoated tablets | | 250.0 | 100.00 |
| Seal coating Ingredients | | | |
| 8 | InstaMoistshield | 7.5 | 3.00 |
| 9 | Isopropyl alcohol | QS | Q.S |
| 10 | Methylene dichloride | QS | Q.S |

-continued

| S. No | Ingredients | Wt. in mg | % W/W |
|---|---|---|---|
| | Enteric coating Ingredients | | |
| 11 | Instacoat EN HPMC P | 22.5 | 8.75 |
| 12 | Isopropyl alcohol | QS | Q.S |
| 13 | Methylene dichloride | QS | Q.S |
| | Wt. of Enteric coating | 30.0 | 11.75 |
| | Wt. of Enteric coated tablets | 280.0 | — |

Example 9

| S. No | Ingredients | Wt. in mg | % W/W |
|---|---|---|---|
| | Dry Mixing | | |
| 1 | Lactoferrin | 100 | 12.72 |
| 2 | Disodium Guanosine 5-Monophosphate (GMP) | 10 | 1.27 |
| 3 | Vitamin C | 500 | 63.61 |
| 4 | Lactose Anhydrous | 150 | 19.08 |
| 5 | Croscarmellose Sodium | 15 | 1.91 |
| 6 | Magnesium Stearate | 5.5 | 0.70 |
| 7 | Colloidal silicon dioxide | 5.5 | 0.70 |
| | Wt. of uncoated tablets | 786.0 | 100.00 |
| | Seal coating Ingredients | | |
| 8 | InstaMoistshield | 20 | 2.75 |
| 9 | Isopropyl alcohol | QS | Q.S |
| 10 | Methylene dichloride | QS | Q.S |
| | Enteric coating Ingredients | | |
| 11 | Instacoat EN HPMC P | 64 | 8.15 |
| 12 | Isopropyl alcohol | QS | Q.S |
| 13 | Methylene dichloride | QS | Q.S |
| | Wt. of Enteric coating | 84.0 | 10.90 |
| | Wt. of Enteric coated tablets | 870.0 | — |

Example 10

| S. No | Ingredients | Wt. in mg | % W/W |
|---|---|---|---|
| | Dry Mixing | | |
| 1 | Lactoferrin | 100 | 40.00 |
| 2 | Guanosine Nucleotide diphosphate (GTP) | 10 | 4.00 |
| 3 | Folic acid | 0.8 | 0.32 |
| 4 | Dicalcium phosphate anhydrous | 104.2 | 41.68 |
| 5 | Sodium starch glycolate | 15 | 6.00 |
| 6 | Magnesium Stearate | 10 | 4.00 |
| 7 | Colloidal silicon dioxide | 10 | 4.00 |
| | Wt. of uncoated tablets | 250.0 | 100.00 |
| | Seal coating Ingredients | | |
| 8 | InstaMoistshield | 7.5 | 3.00 |
| 9 | Isopropyl alcohol | QS | Q.S |
| 10 | Methylene dichloride | QS | Q.S |

-continued

| S. No | Ingredients | Wt. in mg | % W/W |
|---|---|---|---|
| | Enteric coating Ingredients | | |
| 11 | Instacoat EN HPMC P | 22.5 | 8.75 |
| 12 | Isopropyl alcohol | QS | Q.S |
| 13 | Methylene dichloride | QS | Q.S |
| | Wt. of Enteric coating | 30.0 | 11.75 |
| | Wt. of Enteric coated tablets | 280.0 | — |

Example 11

| S. No | Ingredients | Wt. in mg | % W/W |
|---|---|---|---|
| | Dry Mixing | | |
| 1 | Lactoferrin | 100 | 40.00 |
| 2 | Guanosine Nucleotide diphosphate (GTP) | 10 | 4.00 |
| 3 | Vitamin $B_{12}$ | 5 | 2.00 |
| 4 | Dicalcium phosphate anhydrous | 100 | 40.00 |
| 5 | Sodium starch glycolate | 15 | 6.00 |
| 6 | Magnesium Stearate | 10 | 4.00 |
| 7 | Colloidal silicon dioxide | 10 | 4.00 |
| | Wt. of uncoated tablets | 250.0 | 100.00 |
| | Seal coating Ingredients | | |
| 8 | InstaMoistshield | 7.5 | 3.00 |
| 9 | Isopropyl alcohol | QS | Q.S |
| 10 | Methylene dichloride | QS | Q.S |
| | Enteric coating Ingredients | | |
| 11 | Instacoat EN HPMC P | 22.5 | 8.75 |
| 12 | Isopropyl alcohol | QS | Q.S |
| 13 | Methylene dichloride | QS | Q.S |
| | Wt. of Enteric coating | 30.0 | 11.75 |
| | Wt. of Enteric coated tablets | 280.0 | — |

Example 12

| S. No | Ingredients | Wt. in mg | % W/W |
|---|---|---|---|
| | Dry Mixing | | |
| 1 | Lactoferrin | 100 | 40.00 |
| 2 | Disodium Guanosine 5-Monophosphate (GMP) | 10 | 4.00 |
| 3 | Guanosine Nucleotide diphosphate (GDP) | 10 | 4.00 |
| 4 | Vitamin A | 2.5 | 1.00 |
| 5 | Dicalcium phosphate anhydrous | 92.5 | 37.00 |
| 6 | Sodium starch glycolate | 15 | 6.00 |
| 7 | Magnesium Stearate | 10 | 4.00 |
| 8 | Colloidal silicon dioxide | 10 | 4.00 |
| | Wt. of uncoated tablets | 250.0 | 100.00 |
| | Seal coating Ingredients | | |
| 9 | InstaMoistshield | 7.5 | 3.00 |
| 10 | Isopropyl alcohol | QS | Q.S |
| 11 | Methylene dichloride | QS | Q.S |

Example 13

| S. No | Ingredients | Wt. in mg | % W/W |
|---|---|---|---|
| | Dry Mixing | | |
| 1 | Lactoferrin | 100 | 40.00 |
| 2 | Disodium Guanosine 5-Monophosphate (GMP) | 10 | 4.00 |
| 3 | Guanosine Nucleotide diphosphate (GTP) | 10 | 4.00 |
| 4 | Folic acid | 0.8 | 0.32 |
| 5 | Dicalcium phosphate anhydrous | 94.2 | 37.68 |
| 6 | Sodium starch glycolate | 15 | 6.00 |
| 7 | Magnesium Stearate | 10 | 4.00 |
| 8 | Colloidal silicon dioxide | 10 | 4.00 |
| | Wt. of un coated tablets | 250.0 | 100.00 |
| | Seal coating Ingredients | | |
| 9 | InstaMoistshield | 7.5 | 3.00 |
| 10 | Isopropyl alcohol | QS | Q.S |
| 11 | Methylene dichloride | QS | Q.S |
| | Enteric coating Ingredients | | |
| 12 | Instacoat EN HPMC P | 22.5 | 8.75 |
| 13 | Isopropyl alcohol | QS | Q.S |
| 14 | Methylene dichloride | QS | Q.S |
| | Wt. of Enteric coating | 30.0 | 11.75 |
| | Wt. of Enteric coated tablets | 280.0 | — |

Example 14

| S. No | Ingredients | Wt. in mg | % W/W |
|---|---|---|---|
| | Dry Mixing | | |
| 1 | Lactoferrin | 100 | 33.33 |
| 2 | Disodium Guanosine 5-Monophosphate (GMP) | 10 | 3.33 |
| 3 | Microcrystalline cellulose 102 | 109 | 36.33 |
| 4 | Crospovidone | 45 | 15.00 |
| 5 | Croscarmellose Sodium | 25 | 8.33 |
| 6 | Magnesium Stearate | 5.5 | 1.83 |
| 7 | Colloidal silicon dioxide | 5.5 | 1.83 |
| | Wt. of uncoated tablets | 300.0 | 100.00 |
| | Film coating Ingredients | | |
| 8 | Instacoat Universal | 8 | 2.68 |
| 9 | IPA | QS | Q.S |
| 10 | MDC | QS | Q.S |
| | Wt. of Film coating | 8.0 | 2.68 |
| | Wt. of Film coated tablets | 308.0 | — |

Example 15

| S. No | Ingredients | Wt. in mg | % W/W |
|---|---|---|---|
| | Dry Mixing | | |
| 1 | Lactoferrin | 100 | 33.33 |
| 2 | Disodium Guanosine 5-Monophosphate (GMP) | 10 | 3.33 |
| 3 | Guanosine Nucleotide diphosphate (GDP) | 10 | 3.33 |
| 4 | Microcrystalline cellulose 102 | 99 | 33.00 |
| 5 | Crospovidone | 45 | 15.00 |
| 6 | Croscarmellose Sodium | 25 | 8.33 |
| 7 | Magnesium Stearate | 5.5 | 1.83 |
| 8 | Colloidal silicon dioxide | 5.5 | 1.83 |
| | Wt. of uncoated tablets | 300.0 | 100.00 |
| | Film coating Ingredients | | |
| 9 | Instacoat Universal | 8 | 2.68 |
| 10 | IPA | QS | Q.S |
| 11 | MDC | QS | Q.S |
| | Wt. of Film coating | 8.0 | 2.68 |
| | Wt. of Film coated tablets | 308.0 | — |

Example 16

| S. No | Ingredients | Wt. in mg | % W/W |
|---|---|---|---|
| | Dry Mixing | | |
| 1 | Lactoferrin | 100 | 25.00 |
| 2 | Disodium Guanosine 5-Monophosphate (GMP) | 10 | 2.50 |
| 3 | Guanosine Nucleotide diphosphate (GDP) | 10 | 2.50 |
| 4 | Vitamin C | 125 | 31.25 |
| 5 | Microcrystalline cellulose 102 | 74 | 18.50 |
| 6 | Crospovidone | 45 | 11.25 |
| 7 | Croscarmellose Sodium | 25 | 6.25 |
| 8 | Magnesium Stearate | 5.5 | 1.38 |
| 9 | Colloidal silicon dioxide | 5.5 | 1.38 |
| | Wt. of uncoated tablets | 400.0 | 100.00 |
| | Film coating Ingredients | | |
| 10 | Instacoat Universal | 12 | 3.00 |
| 11 | IPA | QS | Q.S |
| 12 | MDC | QS | Q.S |
| | Wt. of Film coating | 12.0 | 3.0 |
| | Wt. of Film coated tablets | 412.0 | — |

Example 17

| S. No | Ingredients | Wt. in mg | % W/W |
|---|---|---|---|
| | Dry Mixing | | |
| 1 | Lactoferrin | 100 | 29.85 |
| 2 | Disodium Guanosine 5-Monophosphate (GMP) | 10 | 2.99 |
| 3 | Vitamin C | 125 | 37.31 |
| 4 | Lactose Anhydrous | 49 | 14.63 |
| 5 | Crospovidone | 25 | 7.46 |
| 6 | Croscarmellose Sodium | 15 | 4.48 |

-continued

| S. No | Ingredients | Wt. in mg | % W/W |
|---|---|---|---|
| 7 | Magnesium Stearate | 5.5 | 1.64 |
| 8 | Colloidal silicon dioxide | 5.5 | 1.64 |
|  | Final Wt. of Capsule | 450.0 | 100 |

Example 18

| S. No | Ingredients | Wt. in mg | % W/W |
|---|---|---|---|
|  | Dry Mixing | | |
| 1 | Lactoferrin | 100 | 42.55 |
| 2 | Disodium Guanosine 5-Monophosphate (GMP) | 10 | 4.26 |
| 3 | Microcrystalline cellulose 102 | 64 | 27.23 |
| 4 | Crospovidone | 15 | 6.38 |
| 5 | Sodium Starch Glycolate | 35 | 14.89 |
| 6 | Magnesium Stearate | 5.5 | 2.34 |
| 7 | Colloidal silicon dioxide | 5.5 | 2.34 |
|  | Final Wt. of Capsule | 295.0 | 100 |

Example 19

| S. No | Ingredients | Wt. in mg | % W/W |
|---|---|---|---|
|  | Dry Mixing | | |
| 1 | Lactoferrin | 100 | 30.77 |
| 2 | Guanosine Nucleotide diphosphate (GDP) | 100 | 30.77 |
| 3 | Microcrystalline cellulose 102 | 74 | 22.77 |
| 4 | Crospovidone | 15 | 4.62 |
| 5 | Croscarmellose sodium | 25 | 7.69 |
| 6 | Magnesium Stearate | 5.5 | 1.69 |
| 7 | Colloidal silicon dioxide | 5.5 | 1.69 |
|  | Final Wt. of Capsule | 400.0 | 100 |

Example 20

| Sr. No | Ingredients | Wt. in mg | % W/W |
|---|---|---|---|
|  | Dry Mixing | | |
| 1 | Lactoferrin | 50 | 14.29 |
| 2 | Disodium Guanosine 5-Monophosphate (GMP) | 5 | 1.43 |
| 3 | Ferrous Bisglycinate eq. 30 mg elemental Iron | 150 | 42.86 |
| 4 | Microcrystalline Cellulose pH 101 | 67.5 | 19.29 |
| 5 | Crospovidone | 15 | 4.29 |
| 6 | Croscarmellose Sodium | 15 | 4.29 |
|  | Binder Solution | | |
| 7 | PVP K-30 | 7.5 | 2.14 |
| 8 | Isopropyl alcohol | QS | QS |
|  | Lubrication | | |
| 9 | Crospovidone | 15 | 4.29 |
| 10 | Croscarmellose Sodium | 15 | 4.29 |
| 11 | Magnesium Stearate | 5 | 1.43 |
| 12 | Colloidal silicon dioxide | 5 | 1.43 |
|  | Wt. of uncoated Tablet | 350.0 | 100.00 |
|  | Seal Coating agent | | |
| 13 | InstaMoistshield | 7 | 2.00 |
| 14 | Isopropyl alcohol | QS | QS |
| 15 | Methylene dichloride | QS | QS |
|  | Enteric coating agent | | |
| 16 | Methacrylate Copolymer | 14.7 | 8.00 |
| 17 | Sodium alginate | 7.88 | |
| 18 | Glycerin | 1.12 | |
| 19 | Talc | 4.3 | |
| 20 | Purified water | QS | QS |
|  | Wt. of Enteric coating | 35.0 | 10.00 |
|  | Wt. of Enteric coated tablets | 385 | — |

Example 21

| Sr. No | Ingredients | Wt. in mg | % W/W |
|---|---|---|---|
|  | Dry Mixing | | |
| 1 | Lactoferrin | 50 | 14.29 |
| 2 | Guanosine Nucleotide diphosphate (GDP) | 10 | 286 |
| 3 | Ferrous Pyrophosphate eq. 30 mg elemental Iron | 130 | 37.14 |
| 4 | Microcrystalline Cellulose pH 101 | 82.5 | 23.57 |
| 5 | Crospovidone | 15 | 4.29 |
| 6 | Croscarmellose Sodium | 15 | 4.29 |
|  | Binder Solution | | |
| 7 | HPMC 6 CPS | 7.5 | 2.14 |
| 8 | Isopropyl alcohol | QS | QS |
| 9 | Purified water | QS | QS |
|  | Lubrication | | |
| 10 | Crospovidone | 15 | 4.29 |
| 11 | Croscarmellose Sodium | 15 | 4.29 |
| 12 | Magnesium Stearate | 5 | 1.43 |
| 13 | Colloidal silicon dioxide | 5 | 1.43 |
|  | Wt. of uncoated Tablet | 350.0 | 100.0 |
|  | Seal Coating agent | | |
| 14 | InstaMoistshield | 7 | 2.00 |
| 15 | Isopropyl alcohol | QS | QS |
| 16 | Methylene dichloride | QS | QS |
|  | Enteric coating agent | | |
| 17 | Shellac | 14.7 | 8.00 |
| 18 | Sodium alginate | 7.88 | |
| 19 | Glycerin | 1.12 | |
| 20 | Talc | 4.3 | |
| 21 | Isopropyl alcohol | QS | QS |
| 22 | Methylene dichloride | QS | QS |
|  | Wt. of Enteric coating | 35.0 | 10.0 |
|  | Wt. of Enteric coated tablets | 385.0 | — |

Example 22

| Sr. No | Ingredients | Wt. in mg | % W/W |
|---|---|---|---|
| | Dry Mixing | | |
| 1 | Lactoferrin | 50 | 12.50 |
| 2 | Disodium Guanosine 5-Monophosphate (GMP) | 5 | 1.25 |
| 3 | Ferrous Bisglycinate eq. 30 mg elemental Iron | 150 | 37.50 |
| 4 | Microcrystalline Cellulose pH 101 | 115 | 28.75 |
| 5 | Crospovidone | 15 | 3.75 |
| 6 | Croscarmellose Sodium | 15 | 3.75 |
| | Binder Solution | | |
| 7 | PVP K-30 | 10 | 2.50 |
| 8 | Folic acid | 0.2 | 0.05 |
| 9 | Isopropyl alcohol | QS | QS |
| | Lubrication | | |
| 10 | Crospovidone | 15 | 3.75 |
| 11 | Croscarmellose Sodium | 15 | 3.75 |
| 12 | Magnesium Stearate | 4.8 | 1.20 |
| 13 | Colloidal silicon dioxide | 5 | 1.25 |
| | Wt. of uncoated Tablet | 400.0 | 100.00 |
| | Seal Coating agent | | |
| 14 | InstaMoistshield | 8 | 2.00 |
| 15 | Isopropyl alcohol | QS | QS |
| 16 | Methylene dichloride | QS | QS |
| | Enteric coating agent | | |
| 17 | Methacrylate Copolymer | 17 | 8.00 |
| 18 | Sodium alginate | 9 | |
| 19 | Glycerin | 1.3 | |
| 20 | Talc | 4.9 | |
| 21 | Purified water | QS | QS |
| | Wt. of Enteric coating | 40.0 | 10.0 |
| | Wt. of Enteric coated tablets | 440.0 | — |

Example 23

| Sr. No | Ingredients | Wt. in mg | % W/W |
|---|---|---|---|
| | Dry Mixing | | |
| 1 | Lactoferrin | 50 | 12.50 |
| 2 | Guanosine Nucleotide diphosphate (GTP) | 10 | 2.50 |
| 3 | Ferrous Pyrophosphate eq. 30 mg elemental Iron | 130 | 32.50 |
| 4 | Microcrystalline Cellulose pH 101 | 127.5 | 31.88 |
| 5 | Crospovidone | 15 | 3.75 |
| 6 | Croscarmellose Sodium | 15 | 3.75 |
| | Binder Solution | | |
| 7 | PVP K-30 | 7.5 | 1.88 |
| 8 | Vitamin $B_{12}$ | 5 | 1.25 |
| 9 | Isopropyl alcohol | QS | QS |
| | Lubrication | | |
| 10 | Crospovidone | 15 | 3.75 |
| 11 | Croscarmellose Sodium | 15 | 3.75 |
| 12 | Magnesium Stearate | 5 | 1.25 |
| 13 | Colloidal silicon dioxide | 5 | 1.25 |
| | Wt. of uncoated Tablet | 400.0 | 100.0 |
| | Seal Coating agent | | |
| 14 | InstaMoistshield | 8 | 2.00 |
| 15 | Isopropyl alcohol | QS | QS |
| 16 | Methylene dichloride | QS | QS |
| | Enteric coating agent | | |
| 17 | Shellac | 17 | 8.00 |
| 18 | Sodium alginate | 9 | |
| 19 | Glycerin | 1.1 | |
| 20 | Talc | 4.9 | |
| 21 | Isopropyl alcohol | QS | QS |
| 22 | Methylene dichloride | QS | QS |
| | Wt. of Enteric coating | 40.0 | 10.0 |
| | Wt. of Enteric coated tablets | 440.0 | — |

Example 24

| Sr. No | Ingredients | Wt. in mg | % W/W |
|---|---|---|---|
| | Dry Mixing | | |
| 1 | Lactoferrin | 50 | 14.29 |
| 2 | Disodium Guanosine 5-Monophosphate (GMP) | 5 | 1.43 |
| 3 | Ferrous Pyrophosphate eq. 30 mg elemental Iron | 130 | 37.14 |
| 4 | Vitamin C | 20 | 5.71 |
| 5 | Microcrystalline Cellulose pH 101 | 60 | 17.14 |
| 6 | Crospovidone | 15 | 4.29 |
| 7 | Croscarmellose Sodium | 15 | 4.29 |
| | Binder Solution | | |
| 8 | PVP K-30 | 15 | 4.29 |
| 9 | Folic acid | 0.2 | 0.06 |
| 10 | Isopropyl alcohol | QS | QS |
| | Lubrication | | |
| 11 | Crospovidone | 15 | 4.29 |
| 12 | Croscarmellose Sodium | 15 | 4.29 |
| 13 | Magnesium Stearate | 4.8 | 1.37 |
| 14 | Colloidal silicon dioxide | 5 | 1.43 |
| | Wt. of uncoated Tablet | 350.0 | 100.0 |
| | Seal Coating agent | | |
| 15 | InstaMoistshield | 7 | 2.00 |
| 16 | Isopropyl alcohol | QS | QS |
| 17 | Methylene dichloride | QS | QS |
| | Enteric coating agent | | |
| 18 | Methacrylate Copolymer | 14.7 | 8.00 |
| 19 | Sodium alginate | 7.88 | |
| 20 | Glycerin | 1.12 | |
| 21 | Talc | 4.3 | |
| 22 | Purified water | QS | QS |
| | Wt. of Enteric coating | 35.0 | 10.0 |
| | Wt. of Enteric coated tablets | 385.0 | — |

Example 25

| Sr. No | Ingredients | Wt. in mg | % W/W |
|---|---|---|---|
| | Dry Mixing | | |
| 1 | Lactoferrin | 50 | 14.29 |
| 2 | Guanosine Nucleotide diphosphate (GDP) | 10 | 2.86 |
| 3 | Ferrous Bisglycinate eq. 30 mg elemental Iron | 150 | 42.86 |
| 4 | Vitamin A | 2.5 | 0.71 |
| 5 | Microcrystalline Cellulose pH 101 | 47.7 | 13.63 |
| 6 | Crospovidone | 15 | 4.29 |
| 7 | Croscarmellose Sodium | 15 | 4.29 |
| | Binder Solution | | |
| 8 | PVP K- 30 | 15 | 4.29 |
| 9 | Vitamin B 12 | 5 | 1.43 |
| 10 | Isopropyl alcohol | QS | QS |
| | Lubrication | | |
| 11 | Crospovidone | 15 | 4.29 |
| 12 | Croscarmellose Sodium | 15 | 4.29 |
| 13 | Magnesium Stearate | 4.8 | 1.37 |
| 14 | Colloidal silicon dioxide | 5 | 1.43 |
| | Wt. of uncoated Tablet | 350.0 | 100.00 |
| | Seal Coating agent | | |
| 15 | InstaMoistshield | 7 | 2.00 |
| 16 | Isopropyl alcohol | QS | QS |
| 17 | Methylene dichloride | QS | QS |
| | Enteric coating agent | | |
| 18 | Methacrylate Copolymer | 14.7 | |
| 19 | Sodium alginate | 7.88 | 8.00 |
| 20 | Glycerin | 1.12 | |
| 21 | Talc | 4.3 | |
| 22 | Purified water | QS | QS |
| | Wt. of Enteric coating | 35.0 | 10.0 |
| | Wt. of Enteric coated tablets | 385.0 | — |

Example 26: Stability Data & Dissolution Data of Example 1 at 40° C., 75% RH

| Sr. No | TEST | Specification | Initial | 1 Month | 3 Months | 6 Months |
|---|---|---|---|---|---|---|
| 1.0 | Description | Light Pink coloured, round shape, biconvex enteric coated tablets | Complies | Complies | Complies | Complies |
| 2.0 | Average weight of tablets | 335 ± 5% | 337 mg | 335.0 mg | 330.9 mg | 335.5 mg |
| 3.0 | Average weight of 20 tablets | 6.7 ± 5% | 6.72 gm | 6.75 gm | 6.70 gm | 6.72 gm |
| 4.0 | Thickness | 4.2 ± 0.2 mm | 4.21 mm | 4.15 mm | 4.13 mm | 4.19 mm |
| 5.0 | Disintegration Test | 0.1 N HCl - Not disintegrate for 2 hours; 6.8 pH Phosphate-disintegrate within 1 hour | Complies | Complies | Complies | Complies |
| 6.0 | Dissolution | | | | | |
| 6.1 | Lactoferrin % of Protein | NLT 75% of the label claim | 91.5% | 91.4% | 91.5% | 92.5% |
| 6.2 | Disodium GMP | NLT 75% of the label claim | 92.4% | 93.4% | 92.4% | 90.5% |
| 7.0 | Assay | | | | | |
| 7.1 | Lactoferrin % of Protein | Between 90.0% and 110.0% of LC | 100.1% | 100.2% | 99.9% | 100.2% |
| 7.2 | Disodium GMP | Between 90.0% and 110.0% of LC | 101.2% | 101.5% | 98.6% | 99.9% |

Example 27: Stability Data & Dissolution Data of Example 4 at 40° C., 75% RH

| Sr. No | TEST | Specification | Initial | 1 Month | 3 Months | 6 Months |
|---|---|---|---|---|---|---|
| 1.0 | Description | Light Pink coloured, round shape, biconvex enteric coated tablets | Complies | Complies | Complies | Complies |
| 2.0 | Average weight of tablets | 235 ± 5% | 237.0 mg | 238.1 mg | 236.5 mg | 237.4 mg |
| 3.0 | Average weight of 20 tablets | 4.7 ± 5% | 4.74 gm | 4.78 gm | 4.7 gm | 4.71 gm |

| Sr. No | TEST | Specification | Initial | 1 Month | 3 Months | 6 Months |
|---|---|---|---|---|---|---|
| 4.0 | Thickness | 4.7 ± 0.2 mm | 4.71 mm | 4.69 mm | 4.74 mm | 4.70 mm |
| 5.0 | Disintegration Test | 0.1 N HCl - Not disintegrate for 2 hours; 6.8 pH Phosphate disintegrate within 1 hour | Complies | Complies | Complies | Complies |
| 6.0 | Dissolution | | | | | |
| 6.1 | Lactoferrin % of Protein | NLT 75% of the label claim | 91.7% | 89.1 % | 92.1% | 89.5% |
| 6.2 | GDP | NLT 75% of the label claim | 90.0% | 88.2% | 94.1% | 93.9% |
| 7.0 | Assay | | | | | |
| 7.1 | Lactoferrin % of Protein | Between 90.0% and 110.0% of LC | 101.9% | 102.7% | 100.3% | 102.1% |
| 7.2 | GDP | Between 90.0% and 110.0% of LC | 99.7% | 103.5% | 99.2% | 103.5% |

Example 28: Stability Data & Dissolution Data of Example 5 at 40° C., 75% RH

| Sr. No | TEST | Specification | Initial | 1 Month | 3 Months | 6 Months |
|---|---|---|---|---|---|---|
| 1.0 | Description | Light Pink coloured, round shape, biconvex enteric coated tablets | Complies | Complies | Complies | Complies |
| 2.0 | Average weight of tablets | 255 ± 5% | 254.8 mg | 255.3 mg | 256.5 mg | 255.1 mg |
| 3.0 | Average weight of 20 tablets | 5.1 ± 5% | 5.1 gm | 5.3 gm | 4.9 gm | 5.4 gm |
| 4.0 | Thickness | 4.1 ± 0.2 mm | 4.14 mm | 4.10 mm | 4.0 mm | 4.11 mm |
| 5.0 | Disintegration Test | 0.1 N HCl - Not disintegrate for 2 hours; 6.8 pH Phosphate - disintegrate within 1 hour | Complies | Complies | Complies | Complies |
| 6.0 | Dissolution | | | | | |
| 6.1 | Lactoferrin % of Protein | NLT 75% of the label claim | 94.2% | 90.7% | 91.2% | 88.6% |
| 6.2 | GTP | NLT 75% of the label claim | 92.1% | 89.1% | 93.4% | 94.3% |
| 7.0 | Assay | | | | | |
| 7.1 | Lactoferrin % of Protein | Between 90.0% and 110.0% of LC | 102.8% | 101.9% | 100.1% | 102.1% |
| 7.2 | GTP | Between 90.0% and 110.0% of LC | 99.9% | 102.9% | 103.4% | 99.7% |

Example 29: Stability Data & Dissolution Data of Example 7 at 40° C., 75% RH

| Sr. No | TEST | Specification | Initial | 1 Month | 3 Months | 6 Months |
|---|---|---|---|---|---|---|
| 1.0 | Description | Light Pink coloured, round shape, biconvex enteric coated tablets | Complies | Complies | Complies | Complies |
| 2.0 | Average weight of tablets | 445 ± 5% | 445.3 mg | 449.7 mg | 450.0 mg | 444.4 mg |
| 3.0 | Average weight of 20 tablets | 8.84 ± 5% | 8.88 gm | 8.80 gm | 8.86 gm | 8.84 gm |

-continued

| Sr. No | TEST | Specification | Initial | 1 Month | 3 Months | 6 Months |
|---|---|---|---|---|---|---|
| 4.0 | Thickness | 5.2 ± 0.2 mm | 5.26 mm | 5.19 mm | 5.27 mm | 5.23 mm |
| 5.0 | Disintegration Test | 0.1 N HCl - Not disintegrate for 2 hours; 6.8 pH Phosphate - disintegrate within 1 hour | Complies | Complies | Complies | Complies |
| 6.0 | Dissolution | | | | | |
| 6.1 | Lactoferrin % of Protein | NLT 75% of the label claim | 88.2% | 91.2% | 92.1% | 91.1% |
| 6.2 | Disodium GMP | NLT 75% of the label claim | 93.4% | 94.8% | 91.4% | 93.6% |
| 6.3 | GDP | NLT 75% of the label claim | 87.1% | 89.1% | 92.8% | 98.9% |
| 6.4 | GTP | NLT 75% of the label claim | 91.4% | 93.6% | 98.9% | 99.6% |
| 7.0 | Assay | | | | | |
| 7.1 | Lactoferrin % of Protein | Between 90.0% and 110.0% of LC | 101.2% | 99.7% | 101.25 | 99.5% |
| 7.2 | Disodium GMP | Between 90.0% and 110.0% | 97.2% | 91.2% | 97.1% | 99.1% |
| 7.3 | Disodium GMP | Between 90.0% and 110.0% of LC | 93.4% | 94.8% | 98.2% | 91.2% |
| 7.4 | GTP | Between 90.0% and 110.0% of LC | 97.1% | 99.1% | 93.4% | 98.8% |

Example 30: Stability Data & Dissolution Data or Example 9 at 40° C., 75% RH

| Sr. No | TEST | Specification | Initial | 1 Month | 3 Months | 6 Months |
|---|---|---|---|---|---|---|
| 1.0 | Description | Light Pink coloured, round shape, biconvex enteric coated tablets | Complies | Complies | Complies | Complies |
| 2.0 | Average weight of tablets | 870 + 5% | 875.3 mg | 871.0 mg | 869.5 mg | 870.5 mg |
| 3.0 | Average weight of 20 tablets | 17.4 + 5% | 17.45 gm | 17.5 gm | 17.11 gm | 17.09 gm |
| 4.0 | Thickness | 10.5 ± 0.2 mm | 10.6 mm | 10.55 mm | 10.4 mm | 10.5 mm |
| 5.0 | Disintegration Test | 0.1 N HCl - Not disintegrate for 2 hours; 6.8 pH Phosphate-disintegrate within 1 hours | Complies | Complies | Complies | Complies |
| 6.0 | Dissolution | | | | | |
| 6.1 | Lactoferrin % of Protein | NLT 75% of the label claim | 89.5% | 89.8% | 90.1% | 92.6% |
| 6.2 | Disodium GMP | NLT 75% of the label claim | 87.1% | 88.0% | 85.3% | 86.5% |
| 6.3 | Vitamin C | NLT 75% of the label claim | 88.0% | 85.3% | 86.5% | 88.0% |
| 7.0 | Assay | | | | | |
| 7.1 | Lactoferrin % of Protein | Between 90.0% and 110.0% of LC | 100.7% | 102.7% | 100.0% | 100.5% |
| 7.2 | Disodium GMP | Between 90.0% and 110.0% or LC | 101.9% | 100.2% | 99.9% | 99.8% |
| 73 | Vitamin C | NLT 90.0% of the label claim | 101.0% | 98.7% | 99.2% | 99.7% |

Example 31: Stability Data & Dissolution Data of Example 14 at 40° C., 75% RH

| Sr. No | TEST | Specification | Initial | 1 Month | 3 Months | 6 Months |
|---|---|---|---|---|---|---|
| 1.0 | Description | Light Pink coloured, round shape, biconvex film coated tablets | Complies | Complies | Complies | Complies |

-continued

| Sr. No | TEST | Specification | Initial | 1 Month | 3 Months | 6 Months |
|---|---|---|---|---|---|---|
| 2.0 | Average weight of tablets | 308 ± 5% | 310.0 mg | 311.0 mg | 315.5 mg | 308.5 mg |
| 3.0 | Average weight of 20 tablets | 6.16 ± 5% | 6.17 gm | 6.17 gm | 6.15 gm | 6.10 gm |
| 4.0 | Thickness | 4.2 ± 0.2 mm | 4.15 mm | 4.18 mm | 4.12 mm | 4.18 mm |
| 5.0 | Disintegration Test | Should disintegrate within 30 minutes | Complies | Complies | Complies | Complies |
| 6.0 | Dissolution | | | | | |
| 6.1 | Lactoferrin % of Protein | NLT 75% of the label claim | 90.2% | 89.8% | 91.3% | 92.3% |
| 6.2 | Disodium GMP | NLT 75% of the label claim | 89.5% | 90.2% | 90.5% | 91.2% |
| 7.0 | Assay | | | | | |
| 7.1 | Lactoferrin % of Protein | Between 90.0% and 110.0% of LC | 102.6% | 103.1% | 103.2% | 101.2% |
| 7.2 | Disodium GMP | Between 90.0% and 110.0% of LC | 104.8% | 98.0% | 97.6% | 97.6% |

Example 32: Stability Data & Dissolution Data of Example 17 at 40° C., 75% RH

| Sr. No | TEST | Specification | Initial | 1 Month | 3 Months | 6 Months |
|---|---|---|---|---|---|---|
| 1.0 | Description | Light Pink coloured granular powder filled in Capsules having red cap and red body | Complies | Complies | Complies | Complies |
| 2.0 | Average weight of Capsules | 450 ± 5% | 450.3 mg | 449.9 mg | 452.0 mg | 451.5 mg |
| 3.0 | Average weight of 20 Capsules | 9.0 ± 5% | 9.0 gm | 8.9 gm | 9.2 gm | 9.1 gm |
| 4.0 | Locking length | 23.4 ± 0.5 mm | 23.4 mm | 23.1 mm | 23.4 mm | 23.7 mm |
| 5.0 | Disintegration Test | NMT 30 Minutes | Complies | Complies | Complies | Complies |
| 6.0 | Dissolution | | | | | |
| 6.1 | Lactofenin % of Protein | NLT 75% of the label claim | 91.4% | 93.6% | 93.4% | 94.8% |
| 6.2 | Disodium GMP | NLT 75% of the label claim | 87.1% | 89.1% | 88.2% | 91.2% |
| 6.3 | Vitamin C | NLT 75% of the label claim | 93.7% | 94.5% | 93.9% | 89.9% |
| 7.0 | Assay | | | | | |
| 7.1 | Lactoferrin % of Protein | Between 90.0% and 110.0% of LC | 100.6% | 100.1% | 102.8% | 98.9% |
| 7.2 | Disodium GMP of LC | Between 90.0% and 110.0% | 101.2% | 99.5% | 101.2% | 99.7% |
| 7.3 | Vitamin C of LC | Between 90.0% and 110.0% | 100.3% | 98.9% | 102.1% | 102.4% |

Example 33: Stability Data & Dissolution Data of Example 20 at 40° C., 75% RH

| Sr. No | TEST | Specification | Initial | 1 Month | 3 Months | 6 Months |
|---|---|---|---|---|---|---|
| 1.0 | Description | White to Off white coloured, round shape, biconvex enteric coated tablets | Complies | Complies | Complies | Complies |
| 2.0 | Average weight of tablets | 385 + 5% | 386.5 mg | 385.8 mg | 384.6 mg | 390.3 mg |
| 3.0 | Average weight of 20 tablets | 7.7 + 5% | 7.72 gm | 7.75 gm | 7.70 gm | 7.73 gm |

| Sr. No | TEST | Specification | Initial | 1 Month | 3 Months | 6 Months |
|---|---|---|---|---|---|---|
| 4.0 | Thickness | 4.7 + 0.2 mm | 4.72 mm | 4.75 mm | 4.73 mm | 4.75 mm |
| 5.0 | Disintegration Test | 0.2 N HCl - Not disintegrate for 2 hours; 6.8 pH Phosphate- disintegrate within 1 hours | Complies | Complies | Complies | Complies |
| 6.0 | Dissolution | | | | | |
| 6.1 | Lactoferrin % of Protein | NLT 75% of the label claim | 91.7% | 92.1% | 93.8% | 94.2% |
| 6.2 | Disodium GMP | NLT 75% of the label claim | 95.3% | 91.8% | 91.8% | 92.3% |
| 6.3 | Ferrous BisglycinatE equivalent to elemental Iron 30.0 mg | NLT 75% of the label claim | 91.5% | 92.6% | 93.1% | 91.5% |
| 7.0 | Assay | | | | | |
| 7.1 | Lactoferrin % of Protein | Between 90.0% and 110.0% of LC | 99.5% | 100.2% | 99.9% | 101.2% |
| 7.2 | Disodium GMP | Between 90.0% and 110.0% of LC | 100.2% | 99.5% | 100.1% | 100.9% |
| 7.3 | Ferrous Bisglycinate equivalent to elemental Iron 30.0 mg | Between 90.0% and 110.0% of LC | 99.9 % | | 99.5 % | 98.4 % |

Example 34: Stability Data & Dissolution Data of Example 22 at 40° C., 75% RH

| Sr. No | TEST | Specification | Initial | 1 Month | 3 Months | 6 Months |
|---|---|---|---|---|---|---|
| 1.0 | Description | White to Off white coloured, round shape, biconvex enteric coated tablets | Complies | Complies | Complies | Complies |
| 2.0 | Average weight of tablets | 440 ± 5% | 440.5 mg | 441.8 mg | 440.3 mg | 442.1 mg |
| 3.0 | Average weight of 20 tablets | 8.8 ± 5% | 8.82 gm | 8.83 gm | 8.81 gm | 8.85 gm |
| 4.0 | Thickness | 5.4 ± 0.2 mm | 5.45 mm | 5.35 mm | 5.42 mm | 5.47 mm |
| 5.0 | Disintegration Test | 0.1 N HCl - Not disintegrate for 2 hours; 6.8 pH Phosphate- disintegrate within 1 hours | Complies | Complies | Complies | Complies |
| 6.0 | Dissolution | | | | | |
| 6.1 | Lactoferrin % of Protein | NLT 75% of the label claim | 90.1% | 91.2% | 90.5% | 91.4% |
| 6.2 | Disodium GMP | NLT 75% of the label claim | 91.2% | 90.3% | 92.1% | 90.8% |
| 6.3 | Ferrous Bisglycinate equivalent to elemental Iron 30.0 mg | NLT 75% of the label claim | 92.2% | 92.9% | 92.1% | 91.5% |
| 6.4 | Folic acid | NLT 75% of the label claim | 89.3% | 90.1% | 90.3% | 89.9% |
| 7.0 | Assay | | | | | |
| 7.1 | Lactoferrin % of Protein | Between 90.0% and 110.0% of LC | 100.5% | 99.4% | 99.5% | 100.2% |
| 7.2 | Disodium GMP | Between 90.0% and 110.0% of LC | 100.2% | 99.5% | 100.1% | 101.9% |
| 7.3 | Ferrous Bisglyeinate equivalent to elemental Iron 30.0 mg | Between 90.0% and 110.0% of LC | 100.1% | 99.9% | 100.9% | 100.4% |
| 7.4 | Folic acid | Not Less than 90.0% of LC | 99.9% | 99.8% | 100.6% | 101.2% |

Example 35: Stability Data & Dissolution Data of Example 25 at 40° C., 75% RH

| Sr. No | TEST | Specification | Duration of Study Initial | 1 Month | 3 Months | 6 Months |
|---|---|---|---|---|---|---|
| 1.0 | Description | Yellow coloured, round shape, biconvex enteric coated tablets | Complies | Complies | Complies | Complies |
| 2.0 | Average weight of tablets | 385 ± 5% | 390 mg | 388 mg | 384 mg | 386 mg |
| 3.0 | Average weight of 20 tablets | 7.7 ± 5% | 7.72 gm | 7.79 gm | 7.68 gm | 7.72 gm |
| 4.0 | Thickness | 4.7 ± 0.2 mm | 4.72 mm | 4.74 mm | 4.76 mm | 4.75 mm |
| 5.0 | Disintegration Test | 0.1 N HCl - Not disintegrate for 2 hours; 6.8 pH Phosphate-disintegrate within 1 hours | Complies | Complies | Complies | Complies |
| 6.0 | Dissolution | | | | | |
| 6.1 | Lactoferrin % of Protein | NLT 75% of the label claim | 90.1% | 90.3% | 91.1% | 90.3% |
| 6.2 | Disodium GMP | NLT 75% of the label claim | 90.9% | 92.1% | 91.9% | 92.1% |
| 6.3 | Ferrous Bisglycinate equivalent to elemental Iron 30.0 mg | NLT 75% of the label claim | 92.5% | 92.6 % | 90.8% | 95.1% |
| 6.4 | Folic acid | NLT 75% of the label claim | 91.3 % | 92.5 % | 92.9% | 91.4% |
| 6.5 | Vitamin C | NLT 75% of the label claim | 90.5% | 89.5% | 91.5% | 92.1% |
| 7.0 | Assay | | | | | |
| 7.1 | Lactoferrin % of Protein | Between 90.0% and 110.0% of LC | 100.5% | 99.4% | 99.5% | 100.2% |
| 7.2 | Disodium GMP | Between 90.0% and 110.0% of LC | 100.2% | 99.5% | 100.1% | 101.9% |
| 7.3 | Ferrous Bisglycinate equivalent to elemental Iron 30.0 mg | Between 90.0% and 110.0% of LC | 100.1% | 99.9% | 100.9% | 100.4% |
| 7.4 | Folic acid | Not Less than 90.0% of LC | 99.9% | 99.8% | 100.6% | 101.2% |
| 7.5 | Vitamin C | Not Less than 90.0% 110 of LC | 101.0% | 98.7% | 99.2% | 99.7% |

Example 36: Animal Study

Screening of pharmaceutical composition/formulation comprising combination of Lactoferrin+Guanosine Nucleotide or a pharmaceutically acceptable salt thereof with or without optional ingredients against Iron deficient Diet (IDD) induced anaemia in rats. For this study different parameters like Hb Level, Hematocrit level, Serum Iron level, Ferroportin level, Serum Ferritin level, Hepcidin level and IL-6 Level were evaluated. The following trials were carried out by taking reference from Wang Xl, Liu S, Xu H, Yan W, Effects of recombinant human lactoferrin on improving the iron status of IDA. Wei Sheng Yan Jiu. 2012 January; 41(1):13-7, 22 and Nora M. El-Sheikh, the Protective Effect of Soybean and Thyme on Iron Deficiency Anemia in Rats, the Egyptian Journal of Hospital Medicine (2008) Vol., 33: 510-520 as available.

72 male Wistar rats (*Rat Rattus*) (6 per group) were maintained in animal house in a light/dark atmosphere based on a 12 hour cycle having temperature and relative humidity in the range of 22±3° C. and 30-70% respectively. To maintain the appropriate conditions, temperature and relative humidity were recorded three times daily. All animals were acclimatized for a minimum period of five days. Animals were maintained in the test setup for minimum 30 minutes once during the acclimatization period to reduce the stress. Animals were weighed on the day of receipt and observed daily for abnormalities if any. Detailed records of acclimatization were also maintained. Rats were housed 6 per cage in clean, sterilized Polypropylene cages. During complete experiment, animals were supplied with the standard certified rat pellet feed (manufactured by Keval sales corporation, Vadodara) and drinking water treated by the reverse osmosis ad libitum. Analysis reports for microbial load and contaminants in feed and water and nutrient content of feed were also retained.

In order to evaluate the activity against IDD induced anaemia, seventy two (72) rats were screened and divided in to twelve groups. For a comparative analysis, groups were divided as normal control (Group 1), disease control (Group 2), treatment groups with individual components (Group 3, Group 4, Group 5, Group 6 and Group 7 as Lactoferrin, Disodium Guanosine monophosphate (GMP), Guanosine diphosphate (GDP), Guanosine triphosphate (GTP) and Vitamin C respectively), test composition/formulation of the present invention (Group 8 as combination of Lactoferrin Disodium GMP, Group 9 as combination of Lactoferrin GDP, Group 10 as combination of Lactoferrin+GTP, Group 1 as combination of Lactoferrin+Disodium GMP+Vitamin C) and reference standard drug (Group 12). Table 1 provides the details of the various groups and treatments conducted in the trial wherein group no. G3 to G12 are treatment groups.

TABLE 1

| S. No. | Group | No. of Animals (Male) | Dose Concentration (mg/kg, p.o.) |
|---|---|---|---|
| 1 | G1 | 6 | Normal Control |
| 2 | G2 | 6 | Disease Control |
| 3 | G3 | 6 | Lactoferrin (20 mg/kg) |
| 4 | G4 | 6 | Disodium Guanosine monophosphate (2 mg/kg) |
| 5 | G5 | 6 | Guanosine diphosphate (2 mg/kg) |
| 6 | G6 | 6 | Guanosine triphosphate (2 mg/kg) |
| 7 | G7 | 6 | Vitamin C (103 mg/kg) |
| 8 | G8 | 6 | Combination of Lactoferrin (20 mg/kg) + Disodium GMP (2 mg/kg) (Ex 1) |
| 9 | G9 | 6 | Combination of Lactoferrin (20 mg/kg) + GDP (2 mg/kg) (Ex 4) |
| 10 | G10 | 6 | Combination of Lactoferrin (20 mg/kg) + GTP (2 mg/kg) (Ex 5) |
| 11 | G11 | 6 | Combination of Lactoferrin (20 mg/kg) + Disodium GMP (2 mg/kg) + Vitamin C (103 mg/kg) (Ex 9) |
| 12 | G12 | 6 | $FeSO_4$ (53 mg/kg) |

Treatment Protocol:

For Induction of Iron Deficient Diet Induced Anaemia Model:

Group nos. 2 to 12 animals under consideration were administered IDD (3 mg Fe/Kg of diet) for the period of 3 weeks, while group 1 animal received Normal pellet diet (35 mg Fe/Kg of diet).

After 3 weeks of respective dietary intervention, the level of Hemoglobin was determined in each animal. Looking at low increase in hemoglobin. Hematocrit % (HCT %) level and serum iron level, further dietary intervention was continued for additional two (2) weeks.

After 5 weeks (35 days) of respective dietary intervention, once again hemoglobin level, HCT % level and serum iron level were analyzed and then, respective drug treatment was started with continuous administration of Iron deficient diets in all groups as mentioned above in Table 1.

After 9 weeks of respective drug treatment (total after 14 weeks from start of the study—98 days), various biochemical parameters were measured to evaluate the effect of respective individual and combination therapy on iron deficient anaemia model (G3 to G12).

Observations:

A. Clinical observations (Daily)
B. Mortality (Daily)
C. Body weight (Initially and then weekly till the end of study)
D. After 3 and 5 weeks of Iron deficient diet supplement
   (i) Hematological parameters (RBC count, Hb Level, Hematocrit % MCV, MCH and MCHC).
   (ii) Serum Iron Level.
E. At the end of 14 weeks of study
   (i) Hematological parameters (RBC count, Hb Level, Hematocrit %, MCV, MCH and MCHC).
   (ii) Biochemical parameters (Serum Iron level, Ferroportin level, Serum Ferritin level, Hepcidin level, IL-6 level).

Statistical Analysis: One way ANOVA followed by Tuckey's test was performed and p value<0.05 is considered to be statistically significant.

Result:

Effect on Body Weight: There were no significant changes observed in body weight of treated and disease control group of animals as compared to the normal control group during the study period.

Cage Side Observation: No significant changes were observed in normal control and treated group of animals as compared to disease control group during the study period.

Mortality: On 21-day one mortality was observed in Group 2; on day 35—one mortality was found in Group 2, one mortality was found in Group 6 and two mortality were found in Group 12.

Hematology: (after 3 Weeks and 5 Weeks of Feed Intervention and after 9 Weeks of Treatment)

After 3 & 5 week: No significant changes were observed in hematology parameter like (RBC count, MCV, MCH and MCHC in disease control (G2) and treated group (G3-G2) of animals as compared to normal control group after administration of iron deficient diet for 3 and 5 weeks respectively.

However, there was significant reduction observed in Hb level and % Hematocrit in disease control (G2) and in treated groups (G3-G12) of animals as compared to normal control group after administration of iron deficient diet for 5 weeks. While the significant change in the said parameters were not observed after administration of iron deficient diet for 3 weeks.

Figure 2:
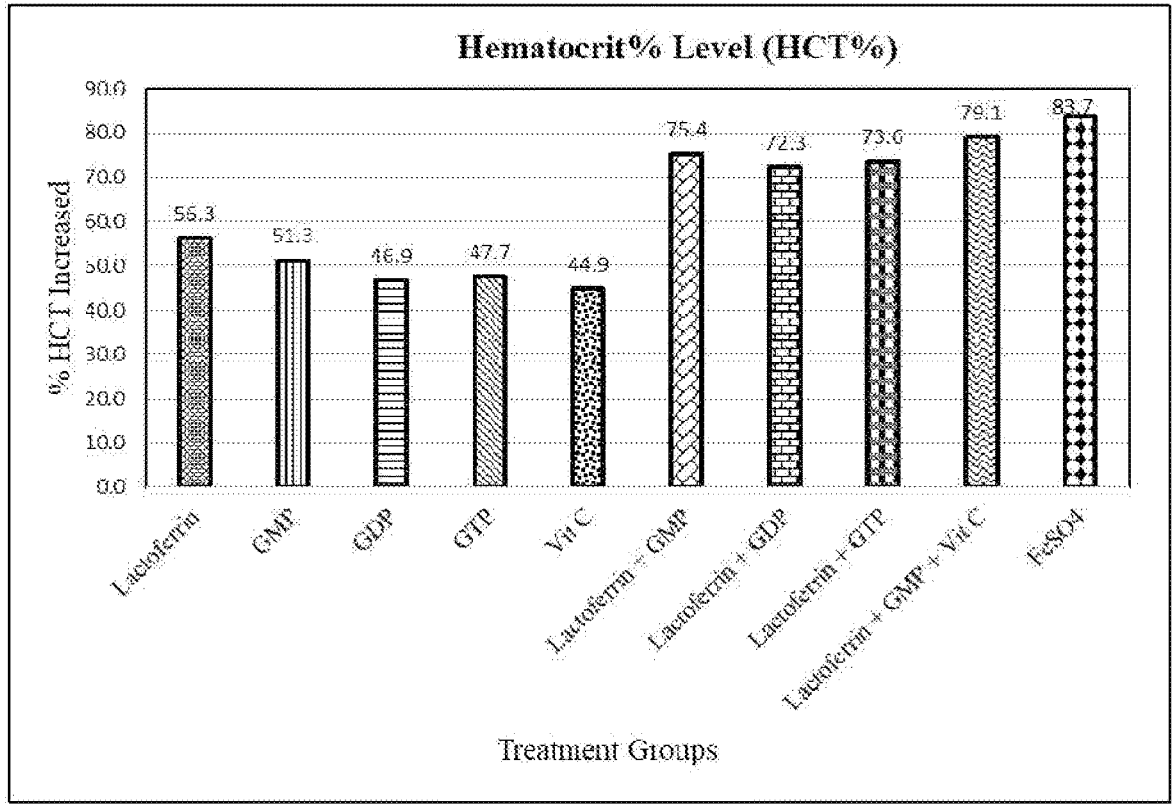
FIG. 2: Effect of test composition/formulation on Hematocrit % level compared to disease control.

After 9 weeks of Treatment: Hb level and % Hematocrit level were increased in all treated groups (G3-G12) of animals as compared to disease control group (G2) after treatment for 9 weeks. More importantly, significant increment in Hb level and % Hematocrit level was observed in G8-G11 (Lactoferrin Combination) and G12 compared to disease control group (G2). (See Table 2 and FIG. 1-2)

There was no significant change observed in other hematology parameter like (RBC count, MCV, MCH and MCHC in all treated group of animals (G3-G12) as compared to disease control group (G2) after treatment for 9 weeks.

Serum Biochemistry:

Serum Iron Level

After 3 & 5 weeks: There was significant reduction observed in scrum Iron level in disease control (G2) and treated groups (G3-G12) as compared to normal control group after administration of iron deficient diet for 5 weeks. While no significant change in the said parameter was observed after administration of iron deficient diet for 3 weeks.

Figure 3:
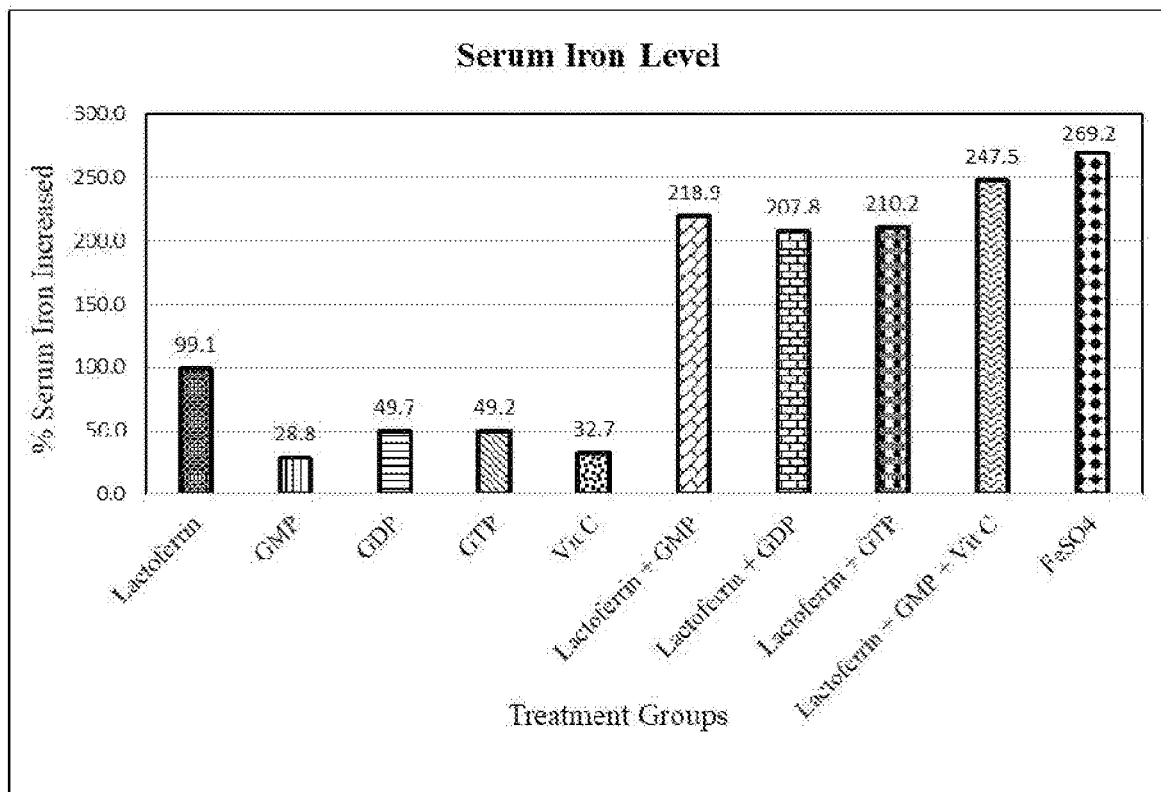
FIG. 3: Effect of test composition/formulation on serum iron level compared to disease control.

After 9 weeks of Treatment: Serum Iron level was increased in all treated groups (G3-G12) of animals as compared to disease control group (G2) after treatment for 9 weeks. More importantly, there was significant increase in the level of serum Iron in case of G8-G11 (Lactoferrin Combination) and G12 ($FeSO_4$) compared to disease control group (2). (See table 2 & FIG. 3)

TABLE 2

Changes in Hemoglobin, Hematocrit and Serum Iron Level

| G. No. | Group ID | Hemoglobin Pre-treatment (mg/dl) Day 35 | Hemoglobin Post-treatment (mg/dl) Day 98 | Hemoglobin % Change compared to Disease control Day 98 | Hematocrit Pre-treatment (%) Day 35 | Hematocrit Post-treatment (%) Day 98 | Hematocrit % Change compared to Disease control Day 98 | Serum IRON Pre-treatment (ppm) Day 35 | Serum IRON Post-treatment (ppm) Day 98 | Serum IRON % Change compared to Disease control Day 98 |
|---|---|---|---|---|---|---|---|---|---|---|
| G1 | Normal | 14.22 | 15.51 | — | 43.19 | 46.87 | — | 9.37 | 10.03 | — |
| G2 | Disease | 8.44 | 6.52 | — | 34.30 | 25.71 | — | 2.98 | 2.67 | — |
| G3 | Lactoferrin | 8.80 | 10.35 | 58.8 | 35.33 | 40.17 | 56.3 | 3.08 | 5.31 | 99.1 |
| G4 | Disodium GMP | 8.54 | 9.18 | 40.8 | 35.35 | 38.89 | 51.3 | 2.82 | 3.43 | 28.8 |
| G5 | GDP | 8.62 | 9.34 | 43.4 | 35.61 | 37.77 | 46.9 | 3.30 | 3.99 | 49.7 |
| G6 | GTP | 8.45 | 9.12 | 39.9 | 35.74 | 37.96 | 11.7 | 3.03 | 3.98 | 49.2 |
| G7 | Vit C | 8.28 | 9.22 | 41.5 | 35.64 | 37.24 | 44.9 | 2.76 | 3.54 | 32.7 |
| G8 | Lectofetrin + Disoditun GMP | 8.36 | 12.52 | 92.1 | 34.84 | 45.09 | 75.4 | 2.67 | 8.50 | 218.9 |
| G9 | Lactoferrin + GDP | 8.40 | 12.08 | 85.3 | 35.98 | 44.29 | 72.3 | 2.73 | 8.20 | 207.8 |
| G10 | Lactoferrin + GTP | 8.36 | 12.04 | 84.7 | 35.48 | 44.62 | 73.6 | 2.83 | 8.27 | 210.2 |
| G11 | Lactoferrin + Disodium GMP + Vit C | 8.74 | 14.89 | 128.5 | 35.98 | 46.04 | 79.1 | 3.38 | 9.26 | 247.5 |
| G12 | FeSO4 | 8.71 | 15.25 | 134.0 | 35.10 | 47.22 | 83.7 | 2.43 | 9.84 | 269.2 |

Serum Biochemical Parameters

After 9 weeks of treatment, various serum biochemical parameters like Hepcidin level, Ferroportin level, Serum Ferritin level and IL-6 level were tested and result obtained is discussed below:

Ferroportin Level

Ferroportin level was decreased in case of disease control group (G2) as compared to normal control group (G1).

Figure 4:
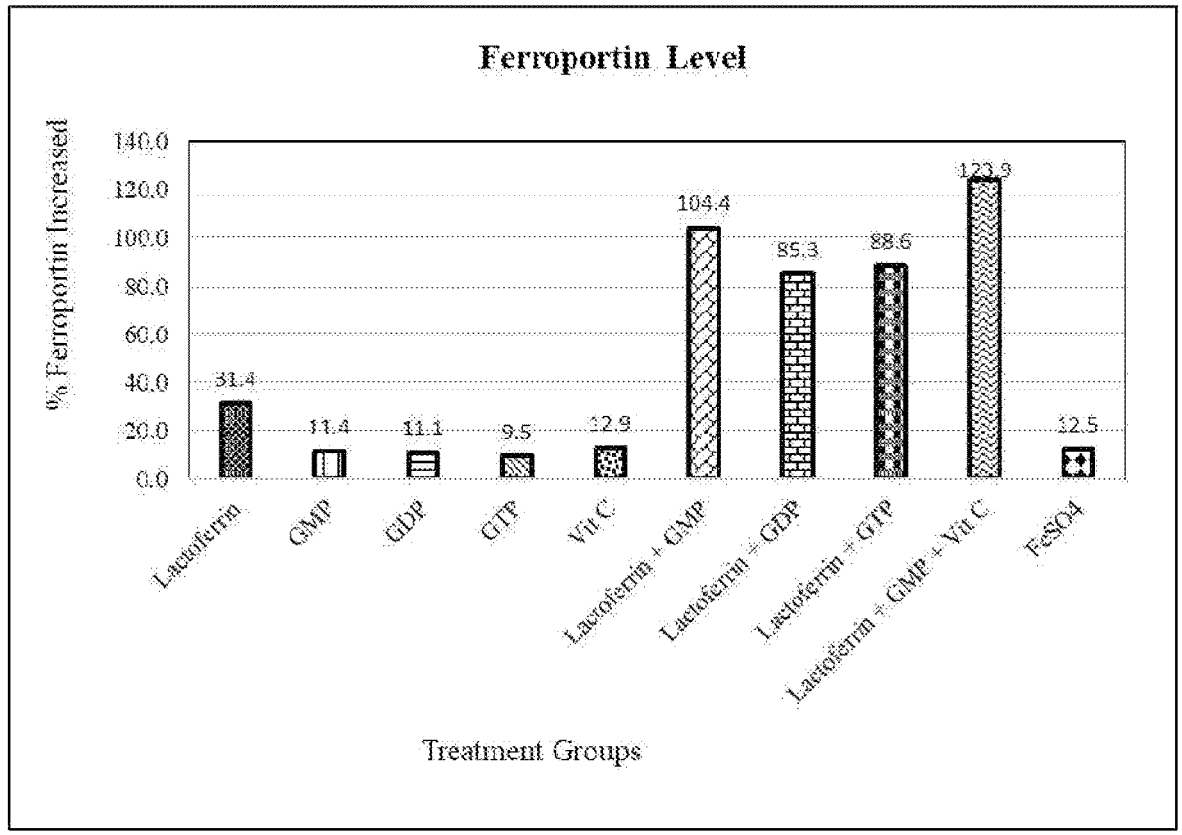
FIG. 4: Effect of test composition/formulation on Ferroportin level compared to disease control.

There was increment in Ferroportin level in case of all treated groups (G3-G12) of animals as compared to disease control group (G2) after treatment of 9 weeks. More importantly, there was significant increase in the level of Ferroportin in case of G8-G11 (Lactoferrin Combination) compared to disease control group (G2). However, there was no significant change observed in Ferroportin level in G12 (FeSO$_4$) compared to disease control group (G2). (See table 3 & FIG. 4)

Serum Ferritin, Hepcidin and IL-6 Level

Figure 5:
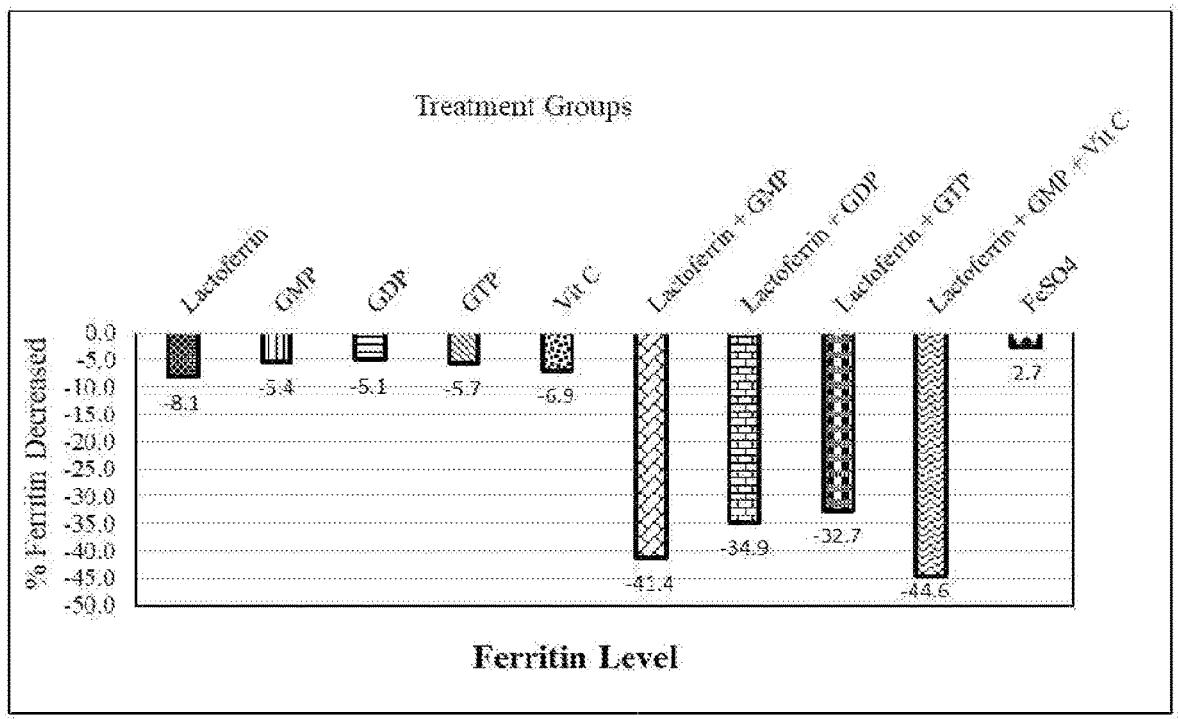
FIG. 5: Effect of test composition/formulation on Ferritin level compared to disease control.
Figure 6:
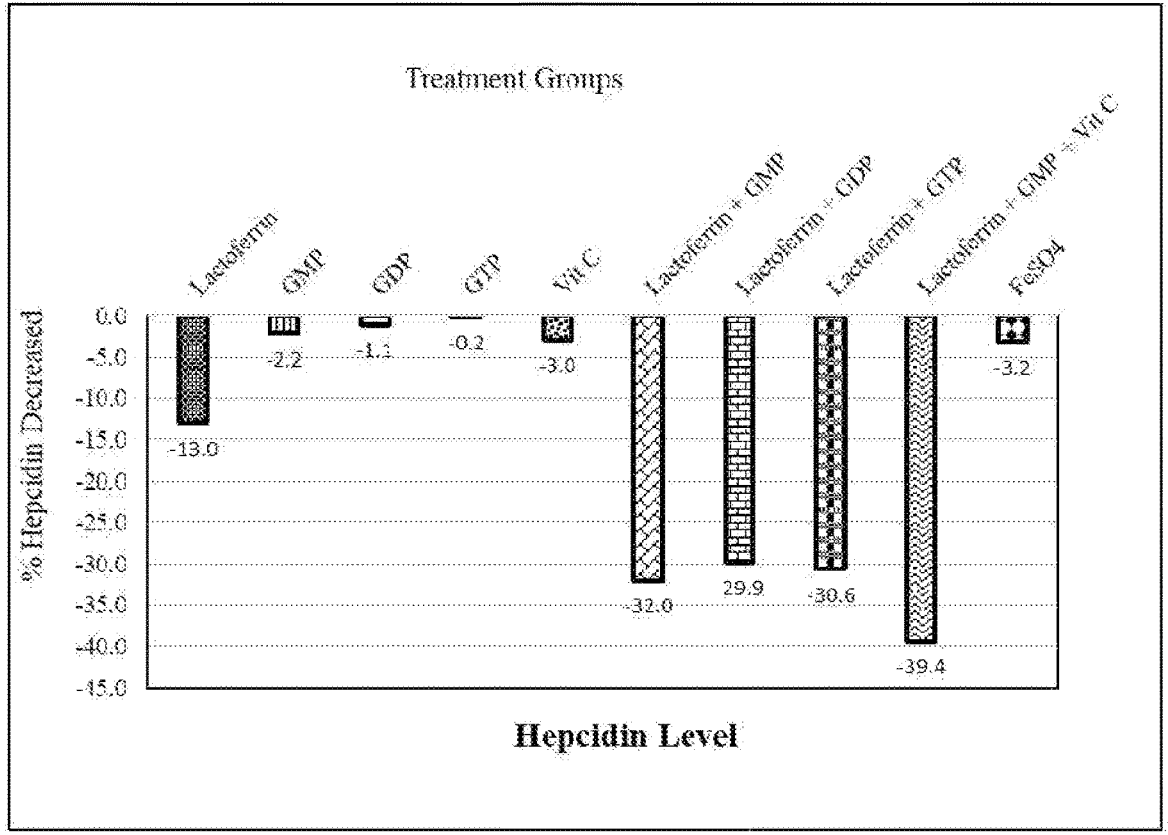
FIG. 6: Effect of test composition/formulation on Hepcidin level compared to disease control.
Figure 7:
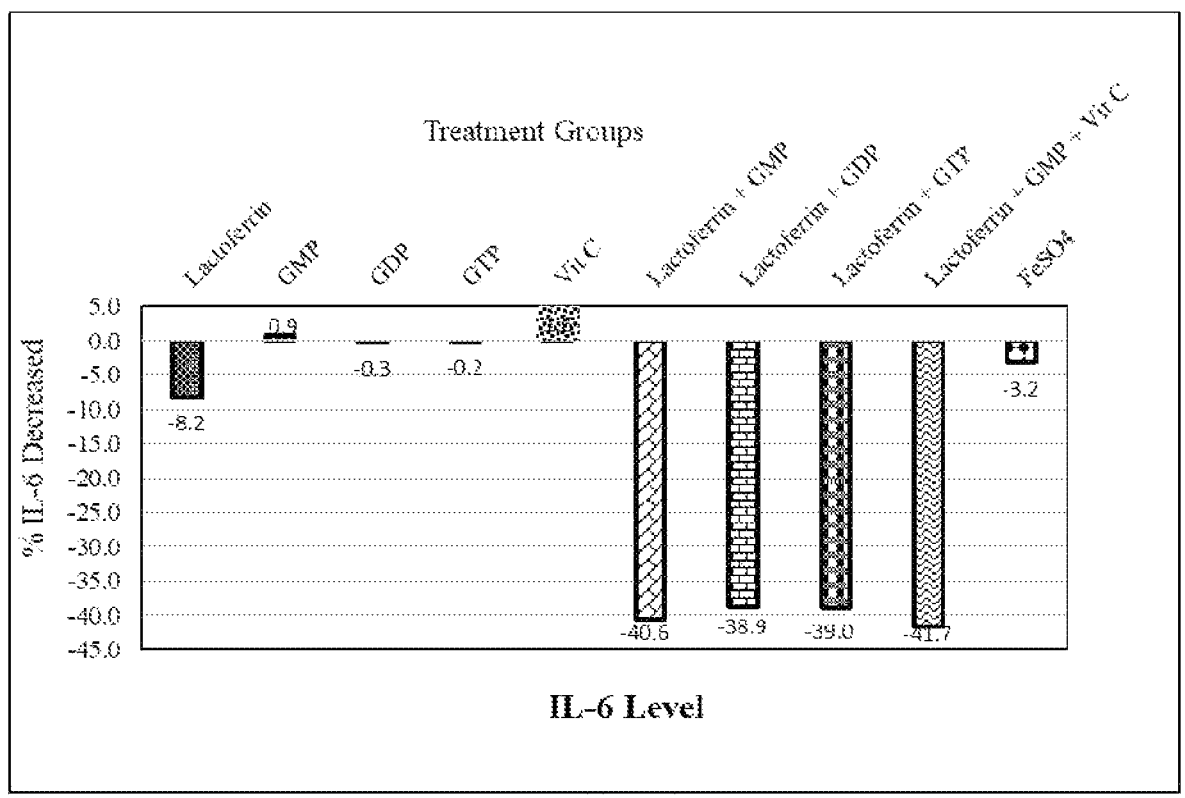
FIG. 7: Effect of test composition/formulation on IL-6 level compared to disease control.

Hepcidin and IL-6 level were significantly increased in case of disease control group (G2) as compared to normal control group (G1), while it has been noted that ferritin value was marginally increased. There was reduction in Serum Ferritin, Hepcidin and IL-6 level observed in case of all treated groups (G3-G12) of animals as compared to disease control group (G2) after treatment of 9 weeks. More importantly, there was significant reduction in the level of Serum Ferritin, Hepcidin and IL-6 level in case of G8-G11 (Lactoferrin Combination) compared to disease control group (G2). However, there was no significant change observed in Serum Ferritin, Hepcidin and IL-6 level in G12 (FeSO$_4$) compared to disease control group (G2). (Sec table 3 & FIG. 5-7)

TABLE 3

Changes in Ferroportin, Ferritin, Hepicidin and IL-6 Level

| G. No. | Group ID | Ferroportin Post-treatment (ng/ml) Day 98 | Ferroportin % Change compared to Disease control Day 98 | Ferritin Post-treatment (ng/ml) Day 98 | Ferritin % Change compared to Disease control Day 98 | Hepcidin Post-tratment (ng/ml) Day 98 | Hepcidin % Change compared to Disease control Day 98 | IL-6 Post-treatment (pg/ml) Day 98 | IL-6 % Change compared to Disease control Day 98 |
|---|---|---|---|---|---|---|---|---|---|
| G1 | Normal | 6.2 | — | 716 | — | 2223 | — | 30.9 | — |
| G2 | Disease | 2.7 | — | 740 | — | 4400 | — | 62.4 | — |
| G3 | Lactoferrin | 3.6 | 31.4 | 680 | −8.1 | 3830 | −13.0 | 57.2 | −8.2 |
| G4 | Disodium GMP | 3.0 | 11.4 | 700 | −5.4 | 4303 | −2.2 | 62.9 | 0.9 |
| G5 | GDP | 3.0 | 11.1 | 702 | −5.1 | 4351 | −1.1 | 62.2 | −0.3 |
| G6 | GTP | 3.0 | 9.5 | 698 | −5.7 | 4392 | −0.2 | 62.2 | −0.2 |
| G7 | Vit C | 3.1 | 12.9 | 689 | −6.9 | 4267 | −3.0 | 63.4 | 1.6 |
| G8 | Lactoferrin + Disodium GMP | 5.5 | 104.4 | 434 | −41.4 | 2991 | −32.0 | 37.1 | −40.6 |
| G9 | Lactoferrin + GDP | 5.0 | 85.3 | 482 | −34.9 | 3084 | −29.9 | 38.1 | −38.9 |

TABLE 3-continued

Changes in Ferroportin, Ferritin, Hepicidin and IL-6 Level

| G. No. | Group ID | Ferroportin Post-treatment (ng/ml) Day 98 | Ferroportin % Change compared to Disease control Day 98 | Ferritin Post-treatment (ng/ml) Day 98 | Ferritin % Change compared to Disease control Day 98 | Hepcidin Post-tratment (ng/ml) Day 98 | Hepcidin % Change compared to Disease control Day 98 | IL-6 Post-treatment (pg/ml) Day 98 | IL-6 % Change compared to Disease control Day 98 |
|---|---|---|---|---|---|---|---|---|---|
| G10 | Lactoferrin + GTP | 5.1 | 88.6 | 498 | −32.7 | 3052 | −30.6 | 38.0 | −39.0 |
| G11 | Lactoferrin + Disodium GMP + Vit C | 6.1 | 123.9 | 410 | −44.6 | 2668 | −39.4 | 36.4 | −41.7 |
| G12 | FeSO4 | 3.0 | 12.5 | 720 | −2.7 | 4260 | −3.2 | 60.4 | −3.2 |

Interpretation and Inference:

The pathologic changes leading to anaemia of chronic disease (ACD) are mediated by several interrelated factors, including interleukin-6 (IL-6), hepcidin, and hypoferremia in Humans. As inflammation increases interleukin-6 production and consequently increase in hepcidin blocks the macrophage iron release as well as intestinal absorption of iron. In order to replicate the conditions of anaemia in experimental animals to resemble with human pathological condition of anaemia, IDD model is the accepted model.

In the present study, anaemia was induced by administering IDD (3 mg Fe/Kg of diet) to Group no. 2 to 12 animals for the period of 5 weeks continued up to 14 weeks. Only normal control group (G1) received Normal pellet diet (35 mg Fe/Kg of diet).

After 5 weeks of administration of IDD in rats, it was observed that there was significant decrease in level of Hb, HCT % and serum iron in case of disease control group and all treatment groups (G2 to G12) as compared to normal control group (G1). This indicates that the disease model was successfully induced condition of anaemia in all the animals.

After 9 weeks of respective drug treatment (total after 14 weeks from start of the study), various hematological parameters (RBC count, Hb Level, Hematocrit %, MCV, MCH and MCHC) and biochemical parameters (Serum Iron level, Ferroportin level, Serum Ferritin level, Hepcidin level, IL-6 level) were measured to evaluate the effect of respective individual and combination therapy on iron deficient anaemia model.

Hematological Parameters

Hb level and % Hematocrit level were increased in all treated groups (G3-G12) of animals as compared to disease control group (G2) after treatment for 9 weeks. More importantly, it needs to be considered that there was a significant increment ($p<0.001$) in the level of Hb and % Hematocrit in G8-G11 (Lactoferrin Combination) and G12 compared to the disease control group (G2).

There was no significant change observed in other hematology parameters like RBC count, MCV, MCH and MCHC in all treated group of animals (G3-G12) as compared to the disease control group (G2) after treatment for 9 weeks.

Biochemical Parameters

Serum iron level was increased in all treated groups (G3-G12) of animals as compared to disease control group (G2) after treatment for 9 weeks. More importantly, it needs to be considered that there was a significant increase ($p<0.001$) in the level of scrum iron in case of G8-G11 (Lactoferrin combination) and G12 (FeSO$_4$) compared to the disease control group (G2).

There was increment in Ferroportin level in case of all treated groups (G3-G12) of animals as compared to disease control group (G2) after treatment of 9 weeks. More importantly, it needs to be considered that there was significant increase ($p<0.001$) in the level of Ferroportin in case of G8-G11 (Lactoferrin Combination) compared to disease control group (G2). However, there was no significant change observed in Ferroportin level in G12 (FeSO$_4$) compared to the disease control group (G2).

Hepcidin and IL-6 level were significantly increased in case of disease control group (G2) as compared to the normal control group (G1), while it has been noted that ferritin value was marginally increased. There was reduction in Serum Ferritin, Hepcidin and IL-6 level observed in case of all treated groups (G3-G12) of animals as compared to disease control group (G2) after treatment of 9 weeks. More importantly, it needs to be considered that there was significant reduction ($p<0.001$) in the level of Serum Ferritin, Hepcidin and IL-6 level in case of G8-G11 (Lactoferrin Combination) compared to disease control group (G2). However, there was no significant change observed in Serum Ferritin, Hepcidin and IL-6 level in G12 (FeSO$_4$) compared to the disease control group (G2).

The results also indicate that the use of combination of Lactoferrin (G8-G11) to an effective dose ameliorates iron deficient anaemia model in rats to a greater extent that individual component (G3-G7).

Hence, among all these treatment groups (G3-G12), G8-G11 group (Lactoferrin combination) exhibited the highest effective in treatment of iron deficient anaemia model in rats as summarized in Table 2-3 below. It indicates that Lactoferrin combinations (G8-G11) provide synergistic effect over individual components and plays an important role in iron deficient anaemic rats.

Regarding Mortality: There was no mortality observed in case of any of the group of animals during treatment of 9 weeks (after 5 weeks) in case of all treatment groups G3-G12.

CONCLUSION

Based on the experimental study conducted on animals, it can be concluded that, all the treatment groups (individual Lactoferrin and its combinations) were effective to treat the anaemia in case of Iron deficient diet induced anaemia model (RAT). However, the level of protection provided by the combination therapy of present invention (includes Lactoferrin+Guanosine Nucleotide(s) or a pharmaceutically acceptable salt thereof) was found to be more effective and superior to individual treatment. The results indicate that Lactoferrin combinations (G8-G11) improve iron status similar to ferrous sulphate (the standard iron supplement) and also provide protective effect against iron-deficiency anaemia. It can be concluded that Group G8-G11 (Lactoferrin combination) exhibit correction of Hepcidin & Inflammatory markers induce Iron deficiency in case of Iron deficient diet induced anaemia model (RAT). The combination therapy of the present invention is also useful in treating neuro-degenerative disorder as well. While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the res tills are contemplated in accordance with the objects and practices of the present invention. It is intended, therefore, that the invention be defined by the scope of the claims which follow and that such claims be interpreted under their broadest reasonable interpretation in view of this specification.

We claim:

1. A pharmaceutical composition comprising a combination of:
   a) Lactoferrin; and
   b) one or more Guanosine Nucleotide or a pharmaceutically acceptable salt thereof, wherein an amount of the Lactoferrin ranges from 5 to 90% by wt. of the composition.

2. The pharmaceutical composition as claimed in claim 1, wherein the Guanosine Nucleotide is selected from Guanosine monophosphate (GMP), Guanosine diphosphate (GDP), Guanosine triphosphate (GTP) or a combination thereof.

3. The pharmaceutical composition as claimed in claim 1, wherein a pharmaceutically acceptable salt of the Guanosine Nucleotide is selected from a hydrochloride, a sulfate, a phosphate, acetate, lactate, citrate, a pantothenate, an ascorbate, a succinate, maleate, fumarate, gluconate, a magnesium salt, potassium, sodium, zinc, the salts of diethanolamine and a combination thereof.

4. The pharmaceutical composition as claimed in claim 1, wherein an amount of the Guanosine Nucleotide ranges from 1 to 75% by wt. of the composition.

5. The pharmaceutical composition as claimed in claim 1, wherein the composition further comprises elemental iron, vitamin C, vitamin A, folic acid, folate, vitamin B or a combination thereof.

6. The pharmaceutical composition as claimed claim 5, wherein an amount of the elemental iron ranges from 30 to 45% by wt. of the composition.

7. The pharmaceutical composition as claimed claim 5, wherein an amount of the vitamin C ranges from 5 to 65% by wt. of the composition.

8. The pharmaceutical composition as claimed in claim 5, wherein an amount of vitamin A ranges from 0.5 to 3% by wt. of the composition.

9. The pharmaceutical composition as claimed in claim 5, wherein an amount of folic acid or folate ranges from 0.05 to 0.75% by wt. of the composition.

10. The pharmaceutical composition as claimed claim 5, wherein an amount of the vitamin B ranges from 1 to 5% by wt. of the composition.

11. The pharmaceutical composition as claimed in claim 1, further comprising pharmaceutically acceptable excipients.

12. The pharmaceutical composition as claimed in claim 11, wherein the pharmaceutically acceptable excipients are selected from a diluent, a binder, a disintegrating agent, a lubricant, a glidant, coating agent, a solvent and combinations thereof.

13. The pharmaceutical composition as claimed in claim 12, wherein an amount of
    the diluent ranges from 5% to 45% by wt. of the composition,
    the binder ranges from 1% to 7% by wt. of the composition,
    the disintegrating agent ranges from 1% to 25% by wt. of the composition,
    the lubricant ranges from 0.5% to 5% by wt. of the composition,
    the glidant ranges from 0.5% to 5% by wt. of the composition,
    the coating agent ranges from 1% to 15% by wt. of the composition, or
    the solvent is quantity sufficient.

14. The pharmaceutical composition as claimed in claim 1, wherein the composition is in the form of a tablet, capsule, pill, hard capsule filled with liquid or solid, soft capsule, powder, granule, sachet, enteric coated tablet or capsule, modified release tablet or capsule.

15. A process for preparation of a composition as claimed in claim 1 comprising:
    (a) individually weighing all the ingredients in separate containers;
    (b) sifting previously weighed Lactoferrin, Guanosine Nucleotide or a pharmaceutically acceptable salt thereof, and optionally adding elemental iron, vitamin C, vitamin A, folic acid, folate or vitamin B, diluent and disintegrating agent separately;
    (c) mixing contents of step (b);
    (d) optionally, preparing a binder solution in a separate container and adding contents to step (c), and sieving the formed granulated wet mass to obtain granules;
    (e) drying the obtained granulates until the level of dryness (LOD) is reduced to between 3.0 to 5.0% w/w;
    (f) sifting the semi-dried granules through a suitable sieve; and
    (g) sifting previously weighed lubricant(s) and glidant(s) separately through a suitable sieve and adding contents to step (f) to obtain the composition.

16. The pharmaceutical composition as claimed in claim 1, wherein the composition is used in treatment of Iron Deficiency Anaemia (IDA) or Anaemia of Inflammation (AOI).

* * * * *